US011540527B2

(12) United States Patent
Buchhorn et al.

(10) Patent No.: US 11,540,527 B2
(45) Date of Patent: Jan. 3, 2023

(54) LACTIC ACID BACTERIA FOR PREPARING FERMENTED FOOD PRODUCTS WITH INCREASED NATURAL SWEETNESS AND HIGH TEXTURE

(71) Applicant: Chr. Hansen A/S, Hoersholm (DK)

(72) Inventors: Gaelle Lettier Buchhorn, Virum (DK); Kim Ib Soerensen, Farum (DK); Mette Pia Junge, Hilleroed (DK)

(73) Assignee: CHR. HANSEN A/S, Hoersholm (DK)

( * ) Notice: Subject to any disclaimer, the term of this patent is extended or adjusted under 35 U.S.C. 154(b) by 1181 days.

(21) Appl. No.: 16/061,638

(22) PCT Filed: Dec. 16, 2016

(86) PCT No.: PCT/EP2016/081361

§ 371 (c)(1),
(2) Date: Jun. 12, 2018

(87) PCT Pub. No.: WO2017/103051

PCT Pub. Date: Jun. 22, 2017

(65) Prior Publication Data

US 2020/0260750 A1 Aug. 20, 2020

(30) Foreign Application Priority Data

Dec. 18, 2015 (EP) .................................... 15201238

(51) Int. Cl.
*A23C 9/123* (2006.01)

(52) U.S. Cl.
CPC ......... *A23C 9/1238* (2013.01); *A23Y 2220/15* (2013.01); *A23Y 2220/29* (2013.01);
(Continued)

(58) Field of Classification Search
CPC .............. A23C 9/1238; A23Y 2220/15; A23Y 2220/29; A23Y 2240/75; C12Y 207/01002; C12Y 207/01006
(Continued)

(56) References Cited

U.S. PATENT DOCUMENTS 10,813,367 B2 10/2020 Garrigues et al.
2012/0164275 A1* 6/2012 Janzen ........... C12Y 207/01006 426/43
2021/0274800 A1* 9/2021 Bloch .................. A23C 21/026

FOREIGN PATENT DOCUMENTS

WO WO-2011/026863 A1 3/2011
WO WO-2011/092300 A1 8/2011
(Continued)

OTHER PUBLICATIONS

Tarantula V.Z., Informatcionno-izdatel'skii' centr Rospatenta, Moskva, 2005, p. 104.
(Continued)

*Primary Examiner* — Brent T O'Hern
(74) *Attorney, Agent, or Firm* — Foley & Lardner LLP

(57) ABSTRACT

The present invention relates to a *Streptococcus thermophilus* strain, wherein the strain is galactose-fermenting, wherein the strain carries a mutation in the DNA sequence of the glcK gene encoding a glucokinase protein, wherein the mutation inactivates the glucokinase protein or has a negative effect on expression of the gene, and wherein the strain carries a mutation in the promoter region of the GalK gene encoding a galactokinase protein.

18 Claims, 1 Drawing Sheet

Specification includes a Sequence Listing.

(52) U.S. Cl.
CPC ... *A23Y 2240/75* (2013.01); *C12Y 207/01002* (2013.01); *C12Y 207/01006* (2013.01)

(58) Field of Classification Search
USPC ............................................................ 426/43
See application file for complete search history.

(56) References Cited

FOREIGN PATENT DOCUMENTS

| | | | | |
|---|---|---|---|---|
| WO | WO-2013/160413 A1 | | 10/2013 | |
| WO | WO-2013160413 A1 | * | 10/2013 | ............ C12N 15/01 |
| WO | WO-2015/193449 A1 | | 12/2015 | |
| WO | WO-2015/193459 A1 | | 12/2015 | |

OTHER PUBLICATIONS

Chervaux et al., "Physiological Study of *Lactobacillus delbrueckii* subsp. *bulgaricus* Strains in a Novel Chemically Defined Medium," Applied and Environmental Microbiology, (Dec. 2000), vol. 66, No. 12, pp. 5306-5311.

Cochu et al., "Genetic and Biochemical Characterization of the Phosphoenolpyruvate: Glucose/Mannose Phosphotransferase System of *Streptococcus thermophiles*," Applied and Environmental Microbiology, (Sep. 2003) vol. 69, No. 9, pp. 5423-5432.

Høier et al., "The Production, Application and Action of Lactic Cheese Starter Cultures," Technology of Cheese Making, Second Edition, (2010) Blackwell Publishing, Oxford, pp. 166-192.

Pool et al., "Natural sweetening of food products by engineering Lactococcus lactis for glucose production," Metabolic Engineering, vol. 8, (2006) pp. 456-464.

Thompson et al., "Lactose Metabolism in *Streptococcus lactis*: Studies with a Mutant Lacking Glucokinase and Mannose-Phosphotransferase Activities," Journal of Bacteriology, (Apr. 1985) vol. 162, No. 1, pp. 217-223.

* cited by examiner

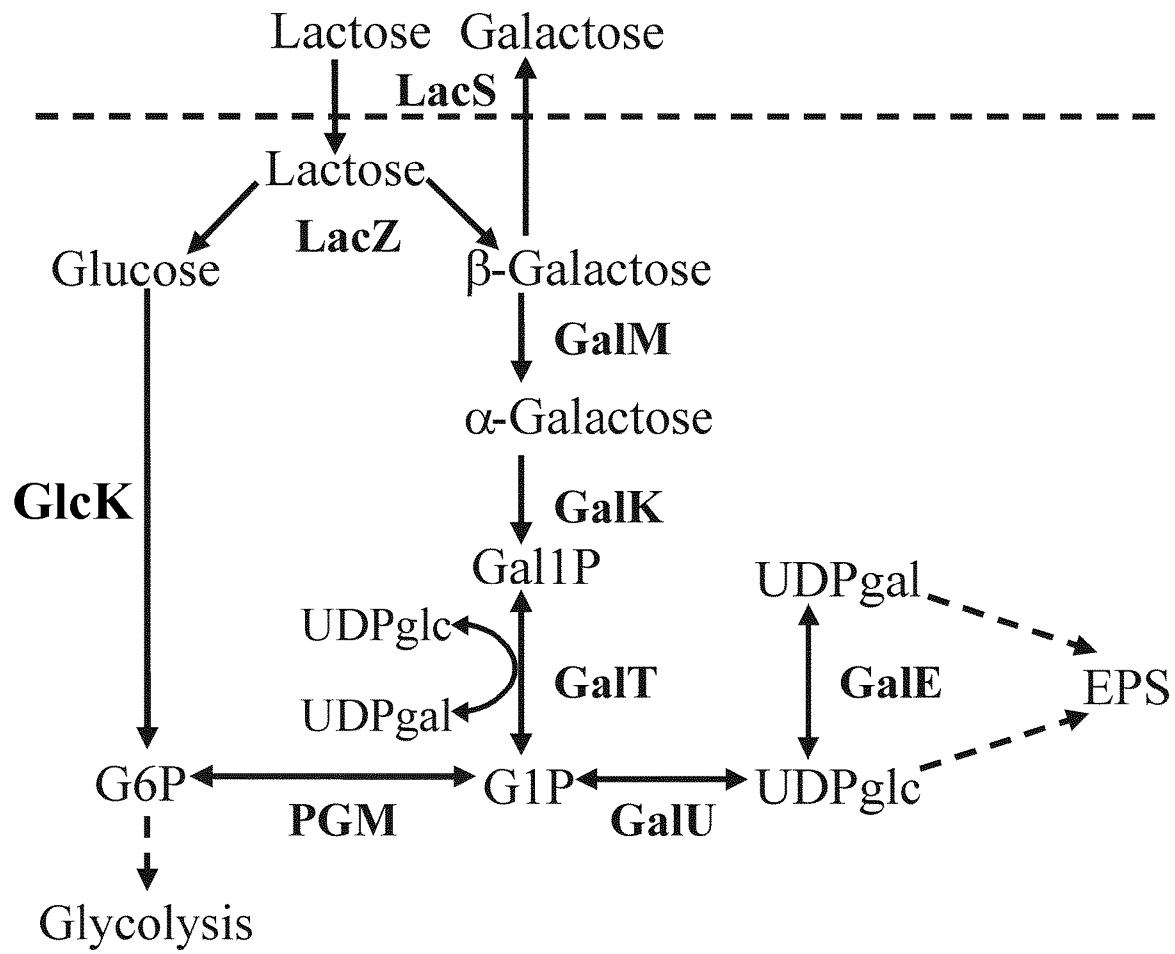
Lactose
Galactose
LacS
Lactose
LacZ
Glucose
β-Galactose
GalM
α-Galactose
GlcK
GalK
Gal1P
UDPgal
UDPglc
GalT
GalE
EPS
UDPgal
G6P
PGM
G1P
GalU
UDPglc
Glycolysis

LACTIC ACID BACTERIA FOR PREPARING FERMENTED FOOD PRODUCTS WITH INCREASED NATURAL SWEETNESS AND HIGH TEXTURE

CROSS-REFERENCE TO RELATED APPLICATIONS

The present application is the U.S. National Stage of International Application PCT/EP2016/081361, filed Dec. 16, 2018, and claims priority to European Patent Application No. 15201238.1, filed Dec. 18, 2015.

FIELD OF INVENTION

The present invention relates to *Streptococcus thermophilus* bacteria strains and cultures with a sweetening property by excretion of high levels of glucose formed by degradation of lactose in combination with a high texturizing property, starter cultures comprising such strains, and dairy products fermented with the cultures. The present invention also relates to a method of producing a fermented milk product and the use of such strains for the preparation of fermented milk products and for increasing the sweetness of fermented milk products while decreasing the lactose content of the fermented milk products.

BACKGROUND OF THE INVENTION

Pure fermented milk products are recognized by a tart or sour taste as a result of the conversion of lactose to lactic acid by lactic acid bacteria during fermentation. They are, therefore, often sweetened by the addition of fruit, honey, sugar or artificial sweeteners to accommodate the customers' desire for a sweeter tasting product.

The food industry has an increasingly high demand for low-calorie sweet-tasting food products in order to help overcome the overweight and obesity problems that have become so prevalent in the last 20 years. Sweetness, usually regarded as a pleasurable sensation, is produced by the presence of sugars and a few other substances. The perception of sugars is very different. Using sucrose as a 100 reference, the sweetness of lactose is 16, of galactose 32 and of glucose 74 (Godshall (1988). Food Technology 42(11): 71-78). Glucose is thus perceived more than 4 times sweeter than lactose while still having approximately the same level of calories.

Sugar in fermented food products is more often being replaced with sweeteners such as aspartame, acesulfame K, sucralose and saccharin which can provide the sweetness with a lower intake of calories. However, the use of artificial sweeteners may result in an off-taste and several studies indicating that the consumption of artificial sweeteners are connected with drawbacks, such as increasing hunger, allergies, cancer etc., have contributed to consumer's preference for fermented milk products which only contain natural sweeteners or, preferably, contain no added sweetener.

Thus, a special challenge lies in developing fermented milk products where the natural (inner) sweetness is high.

The acidity of fermented milk products depend in large part on the lactic acid bacteria present and the process parameters used for preparing the fermented milk product.

Fermentation of the disaccharide lactose is very much studied in lactic acid bacteria because it is the major carbon source in milk. In many species, lactose is cleaved by β-galactosidase into glucose and galactose after uptake. The glucose is phosphorylated by glucokinase to glucose-6-phosphate and fermented via the Embden-Meyerhof-Parnas pathway (glycolysis) by most lactic acid bacteria (FIG. 1).

*Streptococcus thermophilus* is one of the most widely used lactic acid bacteria for commercial thermophilic milk fermentation where the organism is normally used as part of a mixed starter culture, the other component being a *Lactobacillus* sp., e.g. *Lactobacillus delbrueckii* subsp. *bulgaricus* for yoghurt or *Lactobacillus helveticus* for Swiss-type cheese.

The legal definition of yoghurt in many countries requires *Streptococcus thermophilus* alongside *Lactobacillus delbrueckii* subsp. *bulgaricus*. Both species generate desirable amounts of acetaldehyde, an important flavor component in yoghurt.

Lactose and sucrose are fermented more readily by *Streptococcus thermophilus* than their component monosaccharides. In the presence of excess galactose only the glucose portion of the lactose molecule is fermented and galactose accumulates in fermented milk products when *Streptococcus thermophilus* is used. In yoghurt wherein high acid concentrations limit the fermentation, free galactose remains while the free galactose produced in the early stages of Swiss cheese manufacture is later fermented by *Lactobacillus* helveticus.

However, galactose fermenting strains of both *Streptococcus thermophilus* and *Lactobacillus delbrueckii* subsp. *bulgaricus* have been reported by several researchers (Hutkins et al. (1986) J. Dairy Sci. 69(1):1-8; Vaillancourt et al. (2002) J. Bacteriol. 184(3); 785-793) and in WO 2011/026863 (Chr. Hansen) is described a method for obtaining *Streptococcus thermophilus* strains which are galactose fermenting.

In order to meet the requirements of the food industry, it has become relevant to propose new strains, in particular *Streptococcus thermophilus* strains and *Lactobacillus delbrueckii* subsp. *bulgaricus* strains, which provide more natural sweetness without extra calories directly into the fermented product (inner sweetness) by excretion of glucose.

Pool et al. (2006. Metabolic Engineering 8(5); 456-464) discloses *Lactococcus lactis* strain in which the glucose metabolism is completely disrupted by deletion of the genes coding for glucokinase, EII(man/glc) and the newly discovered glucose-PTS EII(cel). The construction method is genetic recombination for generation of all the mutations and the resulting strain is consequently a genetically modified organism (GMO) that at present can not be used in food products.

Thompson et al. (1985. J Bacteriol. 162(1); 217-223) studied the lactose metabolism in *Streptococcus lactis* (today renamed *Lactococcus lactis*). In this work 2-deoxyglucose was used to obtain a mutant in the mannose-PTS system. Subsequently, this mutant was mutagenized using UV mutagenesis followed by screening for glucose-negative colonies by replica plating. In this way a double mutant (mannose PTS and glucokinase) was isolated. This double mutant was used to study the mechanisms involved in the regulation of lactose fermentation by "starter" organisms. These mutants have several disadvantages compared to their parent strain which makes them unsuitable for inclusion in a commercial starter culture. The cell yield of the mutants was half that of the parent strain per mole of lactose fermented and the doubling time was significantly increased in the mutants when grown on lactose. Likewise, the yield of lactic acid was half that of the parent strain per mole of lactose fermented. The behavior of these strains in milk was not analyzed but it is anticipated that the rate of acidification would be significantly reduced.

In addition, *Lactococcus lactis* is generally not chosen for acetaldehyde production and does not contribute to the fulfillment of the requirements for the legal definition of yoghurt.

Chervaux et al. (2000. Appl. And Environ. Microbiol., 66, 5306-5311), studied the physiology of *Lactobacillus delbrueckii* subsp. *bulgaricus* strains in a novel chemically defined medium and isolated 2-deoxyglucose-resistant mutants that were deficient in glucose fermentation. Several different phenotypes were observed and strain-specific effects were reported.

WO2013/160413 discloses *Streptococcus thermophilus* strains and *Lactobacillus delbrueckii* subsp. *bulgaricus* strains with enhanced properties for natural sweetening of food products and for decreasing the lactose content of fermented milk, and method of screening and isolating such strains.

WO2015/193449 discloses a method of producing a fermented milk product with a very low concentration of lactose using a combination of lactase and lactic acid bacteria with a deficiency in glucose metabolism.

WO2015/193459 discloses a method of producing a fermented milk product with a reduced level of post-acidification using a mixture of four lactic acid bacteria strains with a deficiency in glucose metabolism.

WO2011/026863 discloses *Streptococcus thermophilus* strains with improved texturizing properties carrying mutations in the promoter region of the galactokinase (GALK) gene.

WO2011/092300 discloses *Streptococcus thermophilus* strains with improved texturizing properties selected on the basis of phage resistance. The improved texturizing properties arise from an increased production by the bacteria of exopolysaccharides (EPS).

SUMMARY OF INVENTION

The present invention provides *Streptococcus thermophilus* strains, which have enhanced properties for natural sweetening of food products in combination with improved texturizing properties. It has surprisingly been found that it is possible to introduce into *Streptococcus thermophilus* strains both enhanced properties for natural sweetening of food products and improved texturizing properties, and to thereby obtain strains, which have sufficient stability and growth rate so as to be useful for full scale commercial production of fermented milk products. This is surprising since both the enhanced natural sweetening properties and the improved texturing properties each require fundamental changes in the metabolism of the bacteria, which each must be expected to inflict upon the bacteria such an stress so as to render the cells unstable and/or to reduce the cell growth rate to a level unsuitable for commercial production.

In particular, in order to introduce enhanced natural sweetening properties into the *Streptococcus thermophilus* strains of the present invention has been changed so as to make them 1) galactose fermenting, 2) unable to metabolize glucose, e.g. by means of a mutation in the glcK gene and preferable 3) unable to transport glucose across the cell membrane into the cell. Changing the primary carbohydrate source of the bacteria from glucose, which is the preferred carbohydrate source of bacteria, to galactose, which is a considerably less preferred carbohydrate source, would have been expected to impair the growth rate and stability of the cells considerably.

In order to improve the texturizing properties of the *Streptococcus thermophilus* strains of the present invention, the strains have been modified so as to introduce a mutation in the promoter region of the galactokinase (galK) gene, and it has been found that such mutation changes the catabolism of galactose in a manner that leads to increased production of EPS. Again, increased production of EPS would have been expected to impair the growth rate and stability of the cells considerably.

In conclusion, it is surprising that *Streptococcus thermophilus* strains subjected to the combination of changes of metabolic pathways described above have sufficient stability and growth rate so as to be useful for commercial production.

Furthermore, it has surprisingly been found that changing the carbohydrate metabolism of the bacteria with two different objects in mind, i.e. to 1) to increase the EPS production of the cells and 2) to avoid catabolism of glucose and allow catabolism of galactose, does not have any mutual adverse effect on each other. In particular, it would have been expected that it is not possible from the carbohydrate source available at the same time to form both galactose and glucose as well as exopolysaccharide (EPS) in high amounts. Thus, it is surprising that it is in fact possible to improve texturizing properties while at the same time not reducing the sweetening properties.

In particular the present invention relates to the following aspects:

A *Streptococcus thermophilus* strain, wherein the strain is galactose-fermenting, wherein the strain carries a mutation in the DNA sequence of the glcK gene encoding a glucokinase protein, wherein the mutation inactivates the glucokinase protein or has a negative effect on expression of the gene, and wherein the strain carries a mutation in the promoter region of the GalK gene encoding a galactokinase protein, with the proviso that the strain is not the *Streptococcus thermophilus* strain CHCC16731 that was deposited at Deutsche Sammlung von Mikroorganismen und Zellkulturen under accession No. DSM 28889.

A *Streptococcus thermophilus* strain, wherein the strain is selected from the group consisting of the *Streptococcus thermophilus* CHCC19216 strain that was deposited at Deutsche Sammlung von Mikroorganismen und Zellkulturen under accession No. DSM 32227, and a mutant strain derived therefrom, wherein the mutant strain is obtained by using one of the deposited strains as starting material, and wherein the mutant has retained or further improved the texturizing property and the glucose secreting property of said deposited strain.

A composition comprising from $10^4$ to $10^{12}$ CFU/g of a *Streptococcus thermophilus* strain according to the invention.

A method for producing a fermented milk product comprising inoculating and fermenting a milk substrate with at least one *Streptococcus thermophilus* strain according to the invention.

A fermented milk product comprising at least one *Streptococcus thermophilus* strain according to the invention.

Use of a *Streptococcus thermophilus* strain according to the invention for the preparation of a fermented milk product.

Use of a *Streptococcus thermophilus* strain according to the invention for increasing the sweetness of a fermented milk product.

Use of a *Streptococcus thermophilus* strain according to the invention for increasing the texture in a fermented milk product.

Use of a *Streptococcus thermophilus* strain according to the invention for increasing both the sweetness and the texture in a fermented milk product.

Use of a *Streptococcus thermophilus* strain according to the invention in combination with a *Lactobacillus delbrueckii* subsp. *bulgaricus* strain for the preparation of a fermented milk product.

Use of a *Streptococcus thermophilus* strain according to the invention in combination with a *Lactobacillus delbrueckii* subsp. *bulgaricus* strain for increasing the sweetness of a fermented milk product.

Use of a *Streptococcus thermophilus* strain according to the invention in combination with a *Lactobacillus delbrueckii* subsp. *bulgaricus* strain for increasing the texture in a fermented milk product.

Use of a *Streptococcus thermophilus* strain according to the invention in combination with a *Lactobacillus delbrueckii* subsp. *bulgaricus* strain for increasing both sweetness and the texture in a fermented milk product.

A fermented milk product according to the invention for use in avoiding symptoms of lactose intolerance.

BRIEF DESCRIPTION OF THE DRAWINGS

FIG. 1 is a schematic representation of lactose catabolism in *Streptococcus thermophilus*. GlcK, glucokinase; LacS, lactose transporter; LacZ, β-galactosidase; GalM, mutarotase; GalK, galactokinase; GalT, galactose-1-phosphate uridyltransferase; GalE, UDP-glucose 4 epimerase; Gal1P, galactose-1-phosphate.

DETAILED DISCLOSURE OF THE INVENTION

Definitions

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pediococcus* spp., *Brevibacterium* spp., *Enterococcus* spp. and *Propionibacterium* spp. Lactic acid bacteria, including bacteria of the species *Lactobacillus* sp. and *Streptococcus thermophilus*, are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product. Such cultures are in general referred to as "starter cultures" or "starters".

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

In connection with the present invention, the expression "increasing the sweetness" means an increase in sweetness as compared to the sweetness produced by a mother strain not carrying a mutation in the DNA sequence of the glcK gene encoding a glucokinase protein, wherein the mutation inactivates the glucokinase protein or has a negative effect on expression of the gene.

In connection with the present invention, the expression "increasing the texture" means an increase in texture as compared to the texture produced by a mother strain not carrying a mutation in the promoter region of the GalK gene.

Texturizing Property of the *Streptococcus thermophilus* Strains

In connection with the present invention the improved texturizing property of the *Streptococcus thermophilus* strain of the invention means that the *Streptococcus thermophilus* strain carries a mutation in the promoter region of the GalK gene.

The mutation in the promoter region of the GalK gene may be obtained by any conventional method for obtaining such mutation.

In one embodiment of the invention, the *Streptococcus thermophilus* strain carries a mutation in the promoter region of the GalK gene downstream of the −10 promoter box, also known as the Pribnow box (TACGATS). In a more particular embodiment of the invention the mutation in the promoter region of the GalK gene is a mutation in the position 3 nucleotides downstream of the −10 promoter box, in particular a mutation of C in the position 3 nucleotides downstream of the −10 promoter box into A.

In another embodiment of the inventions, the mutation in the promoter region of the GalK gene is a mutation in the −10 promoter box. In a particular embodiment of the invention, the C of the −10 promoter box is replaced with a nucleotide selected from the group consisting of A, G and T, in particular a group consisting of A and T. In a more particular embodiment of the invention, the C of the −10 promoter box is replaced with T.

The *Streptococcus thermophilus* strain of the invention generates a shear stress in fermented milk greater than about 40 Pa, preferably greater than 43 Pa, more preferably greater than 47 Pa, and most preferably greater than 50 Pa, measured after 12 hours of growth at 37 degrees C., e.g. inoculated in an amount of at least 10E4 cells per ml of milk.

In the present invention the expression "GalK gene encoding a galactokinase" means any DNA sequence of a *Streptococcus thermophilus* encoding a protein having galactokinase activity. A galactokinase catalyzes the reaction converting galactose to galactose-1-phosphate, cf. FIG. 1.

Texture (shear stress) may be analyzed by use of the following assay: Seven days after incubation, the fermented milk was brought to 13° C. and stirred gently by means of a stick fitted with a bored disc until homogeneity of the sample. The rheological properties of the sample were assessed on a rheometer (Anton Paar Physica ASC/DSR301 Rheometer (Autosampler), Anton Paar® GmbH, Austria) using the following settings:

Wait time (to rebuild to somewhat original structure) 5 minutes without oscillation or rotation Oscillation (to measure G' and G" for calculation of G*) γ=0.3%, frequency (f)=[0.5 . . . 8] Hz 6 measuring points over 60 s (one every 10 s)

Rotation (to measure shear stress at 300 1/s etc.) $\dot{\gamma}$=[0.2707-300] 1/s and $\dot{\gamma}$=[275-0.2707] 1/s 21 measuring point over 210 s (on every 10 s) going up to 300 1/s and 21 measuring points over 210 s (one every 10 s) going down to 0.2707 1/s For further analysis the shear stress at 300 1/s was chosen.

Method of Producing a Texturizing *Streptococcus thermophilus* Strain

One method of producing a *Streptococcus thermophilus* strain having a higher shear stress and/or gel firmness than the mother strain when the bacteria are used for fermenting milk comprises the steps of:

a) Providing a lactic acid *Streptococcus thermophilus* strain (the mother strain), and b) introducing a mutation in the GalK gene of the strain.

The method of the invention may further comprise one or more further steps:

c1) screening for a mutant strain which generates texture, such as a strain which generates more texture than the mother stain, or increases the texture of a milk substrate, and c2) screening for a mutant strain having Gal+ phenotype, such as improved galactose degrading/fermenting activity compared to the mother stain.

A second method of producing a *Streptococcus thermophilus* strain having a higher shear stress and/or gel firmness than the mother strain when the bacteria are used for fermenting milk, comprises the steps of:

a) Providing a *Streptococcus thermophilus* strain (the mother strain), a1) Exposing the lactic bacterial strain to a bacteriophage, e.g. a bacteriophage which is able to lyse the mother strain, such as a phage selected from the group consisting of CHPC658, CHPC1057, CHPC1089 and CHPC1152, and b) Isolating a mutant strain of the mother strain, which mutant strain is resistant against the phage (or which strain is not lysed by the phage).

Also, the method may comprise the steps of:

a) Providing a *Streptococcus thermophilus* strain (the mother strain);

a1) Exposing the lactic bacterial strain to a bacteriophage, e.g. a bacteriophage which is able to lyse the mother strain, such as a phage selected from the group consisting of CHPC658, CHPC1057, CHPC1089 and CHPC1152;

a2) Incubating the exposed bacterial cells in a growth medium; and b) isolating a mutant strain of the mother strain, which mutant strain is not lysed by the bacteriophage The method may comprise the step of:

c) mutating (e.g. by chemical treatment or radiation treatment, or by means of genetic engineering techniques) the mother strain, e.g. before, during or after step a1).

Also, the method may comprise the step of:

d) introducing a mutation in the galK gene or the galK regulatory sequence (e.g. promoter) of the strain (e.g. by chemical treatment or radiation treatment, or by means of genetic engineering techniques), e.g. before, during or after step c), or before, during or after step a1).

In an interesting embodiment, the method comprises the steps of:

Providing a *Streptococcus thermophilus* strain (the mother strain),

Mutating (e.g. by chemical treatment or radiation treatment, or by means of genetic engineering techniques) the mother strain, Exposing the resulting lactic bacterial strain to a bacteriophage, e.g. a bacteriophage which is able to lyse the mother strain, such as a phage selected from the group consisting of CHPC658, CHPC1057, CHPC1089 and CHPC1152, Incubating the exposed bacterial cells in a growth medium, and isolating a mutant strain of the mother strain, which mutant strain is not lysed by the bacteriophage;

Sweetening Property of the *Streptococcus thermophilus* Strains

In some countries, the legal definition of yoghurt requires the presence of both *Streptococcus thermophilus* and *Lactobacillus delbrueckii* subsp. *bulgaricus*. Both species generate desirable amounts of acetaldehyde, an important flavor component in yoghurt.

Cheese, such as Mozzarella and Pizza cheese as well as Feta, can also be prepared by fermentation using both *Streptococcus thermophilus* and *Lactobacillus delbrueckii* subsp. *bulgaricus* (Høier et al. (2010) in The Technology of Cheese making, $2^{nd}$ Ed. Blackwell Publishing, Oxford; 166-192).

In order to meet the requirements of the food industry, it has become desirable to develop new strains, in particular *Lactobacillus delbruckii* subsp. *bulgaricus* strains and *Streptococcus thermophilus* strains, which produce more natural sweetness directly in the fermented product (inner sweetness) without contributing extra calories.

*Streptococcus thermophilus* is one of the most widely used lactic acid bacteria for commercial milk fermentation where the organism is normally used as part of a mixed starter culture, the other component being a *Lactobacillus* sp., e.g. *Lactobacillus delbrueckii* subsp. *bulgaricus* for yoghurt and *Lactobacillus helveticus* for Swiss-type cheese.

Lactose and sucrose are fermented more readily by *Streptococcus thermophilus* than their component monosaccharides. Only the glucose portion of the lactose molecule is fermented by *Streptococcus thermophilus* and galactose accumulates in fermented milk products when *Streptococcus thermophilus* is used. In yoghurt, wherein high acid concentrations limit the fermentation, free galactose remains while the free galactose produced in the early stages of Swiss cheese manufacture is later fermented by *Lactobacillus helveticus. Lactococcus lactis* found in many starter cultures used for cheese manufacture is also capable of consuming the galactose produced by *Streptococcus thermophilus.*

In order to ensure *Streptococcus thermophilus* strains with a growth performance as optimal as possible, the present inventors have exposed galactose-fermenting strains of *Streptococcus thermophilus* to the selective agent 2-deoxyglucose. Typically 2-deoxyglucose resistant mutants have mutations in the gene encoding glucokinase and in genes coding for glucose transport. The isolated mutant, CHCC16731, which are resistant to 2-deoxyglucose have a mutation in its glucokinase (glcK) gene. In addition to a mutation in the glucokinase gene, the present inventors found that CHCC16731 and CHCC19216 both have a mutation which means that secreted glucose is not transported back into the cells again. Although not part of the scope of the present invention, strain 16731 is used herein for illustration of the strain of the invention, in particular with respect to the specific mutations a strain of the present invention may contain.

Surprisingly, such mutants alone are still fully capable of acidifying milk although acidification time to pH 5 is delayed by 2-5 hours. They are therefore as such useful in fermented milk applications and they have preserved the ability of the mother strains to clot the milk which is characteristic of yoghurt. Additionally, it was found that the mutants excreted a high level of glucose, when 9.5% B-milk with 0.05% sucrose was inoculated with the mutants and fermented at 40° C. for at least 20 hours. At the same time, very low levels of lactose remain in the fermented milk. Therefore, the use of such strains for producing fermented milk products may have an importance for people with lactose intolerance.

Consequently, the final fermented milk has an increased inner sweetness index calculated as described by Godshall (1988. Food Technology 42(11):71-78).

In one aspect of the present invention, the *Streptococcus thermophilus* strain is a galactose-fermenting mutant strain of *Streptococcus thermophilus*, wherein the mutant strain carries a mutation in the DNA sequence of the glcK gene encoding a glucokinase protein, wherein the mutation inactivates the encoded glucokinase protein or has a negative effect on expression of the gene. Methods for measuring the level of glucokinase activity or the level of expression of the glucokinase gene are readily known (Porter et al. (1982) Biochim. Biophys. Acta, 709; 178-186) and include enzyme assays with commercially available kits and transcriptomics or quantitative PCR using materials which are readily available.

In a preferred embodiment of the invention, the *Streptococcus thermophilus* strain of the invention is 2-deoxyglucose resistant.

A bacterial "strain" as used herein refers to a bacterium which remains genetically unchanged when grown or multiplied. A multiplicity of identical bacteria is included.

The term "galactose-fermenting *Streptococcus thermophilus* strains" as used herein refers to *Streptococcus thermophilus* strains which are capable of growth on/in M17 medium+2% galactose. The galactose-fermenting *Streptococcus thermophilus* strains are defined herein as *Streptococcus thermophilus* strains which lower the pH of M17 broth containing 2% galactose as sole carbohydrate to 5.5 or lower when inoculated from an overnight culture at 1% and incubated for 24 hours at 37° C.

The term "the mutation inactivates the glucokinase protein" as used herein refers to a mutation which results in an "inactivated glucokinase protein", a glucokinase protein which, if present in a cell, is not able to exert its normal function as well as mutations which prevent the formation of the glucokinase protein or result in degradation of the glucokinase protein.

In particular, an inactivated glucokinase protein is a protein which compared to a functional glucokinase protein is not able to facilitate phosphorylation of glucose to glucose-6-phosphate or facilitates phosphorylation of glucose to glucose-6-phosphate at a significantly reduced rate. The gene encoding such an inactivated glucokinase protein compared to the gene encoding a functional glucokinase protein comprises a mutation in the open reading frame (ORF) of the gene, wherein said mutation may include, but is not limited to, a deletion, a frameshift mutation, introduction of a stop codon or a mutation which results in an amino acid substitution, which changes the functional properties of the protein, or a promoter mutation that reduces or abolishes transcription or translation of the gene.

In preferred embodiments the mutation reduces the activity (the rate of phosphorylation of glucose to glucose-6-phosphate) of the glucokinase protein with at least 50%, such as at least 60%, such as at least 70%, such as at least 80%, such as at least 90%.

The glucokinase activity can be determined by the glucokinase enzymatic assays as described by Pool et al. (2006. Metabolic Engineering 8; 456-464).

The term "functional glucokinase protein" as used herein refers to a glucokinase protein which, if present in a cell, facilitates phosphorylation of glucose to glucose-6-phosphate. In particular, a functional glucokinase protein may be encoded by a gene comprising an ORF which has a sequence corresponding to position 1-966 in SEQ ID NO. 1 or a sequence which has at least 85% identity, such as at least 90% identity, such as at least 95% identity, such as at least 98% identity, such as at least 99% identity, to the sequence corresponding to position 1-966 of SEQ ID NO. 1.

The percent identity of two sequences can be determined by using mathematical algorithms, such as the algorithm of Karlin and Altschul (1990. Proc. Natl. Acad. Sci. USA 87; 2264), the modified algorithm described in Karlin and Altschul (1993. Proc. Natl. Acad. Sci. USA 90; 5873-5877); the algorithm of Myers and Miller (1988. CABIOS 4; 11-17); the algorithm of Needleman and Wunsch (1970. J. Mol. Biol. 48; 443-453); and algorithm of Pearson and Lipman (1988. Proc. Natl. Acad. Sci. USA 85; 2444-2448). Computer software for the determination of nucleic acid or amino acid sequence identity based on these mathematical algorithms is also available. For example, the comparison of nucleotide sequences can be performed with the BLASTN program, score=100, wordlength=12. The comparison of amino acid sequences can be performed with the BLASTX program, score=50, wordlength=3. For the remaining parameters of the BLAST programs, the default parameters can be used.

In many countries the use of genetically modified organisms (GMOs) for fermented milk products is not accepted. The present invention instead provides for naturally occurring or induced mutant strains which can provide a desirable accumulation of glucose in the fermented milk product.

Thus, in a much preferred embodiment of the present invention the mutant strain is a naturally occurring mutant or an induced mutant.

A "mutant bacterium" or a "mutant strain" as used herein refers to a natural (spontaneous, naturally occurring) mutant bacterium or an induced mutant bacterium comprising one or more mutations in its genome (DNA) which are absent in the wild type DNA. An "induced mutant" is a bacterium where the mutation was induced by human treatment, such as treatment with chemical mutagens, UV— or gamma radiation etc. In contrast, a "spontaneous mutant" or "naturally occurring mutant" has not been mutagenized by man. Mutant bacteria are herein, non-GMO (non-genetically modified organism), i.e. not modified by recombinant DNA technology.

"Wild type strain" refers to the non-mutated form of a bacterium, as found in nature.

Terms such as "strains with a sweetening property", "strains which can provide a desirable accumulation of glucose in the fermented milk product" and "strains with enhanced properties for natural sweetening of food products" are used interchangeably herein to characterize an advantageous aspect of using the strains of the present invention in fermentation of milk products.

In a preferred embodiment, the mutant strain of *Streptococcus thermophilus* according to the invention increases the amount of glucose in 9.5% B-milk to at least 5 mg/mL when inoculated into the 9.5% B-milk at a concentration of $10^6$-$10^7$ CFU/ml and grown at 40° C. for at least 20 hours.

In another preferred embodiment, the mutant strain of *Streptococcus thermophilus* according to the invention increases the amount of glucose in 9.5% B-milk with 0.05% sucrose to at least 5 mg/mL when inoculated into the 9.5% B-milk with 0.05% sucrose at a concentration of $10^6$-$10^7$ CFU/ml and grown at 40° C. for at least 20 hours.

In the present context, 9.5% B-milk is boiled milk made with reconstituted low fat skim milk powder to a level of dry matter of 9.5% and pasteurized at 99° C. for 30 min. followed by cooling to 40° C.

In more preferred embodiments of the invention the mutant strain leads to an increase in the amount of glucose to at least 6 mg/mL, such as at least 7 mg/mL, such as at least 8 mg/mL, such as at least 9 mg/ml, such as at least 10 mg/ml, such as at least 11 mg/ml, such as at least 12 mg/ml, such as at least 13 mg/ml, such as at least 14 mg/ml, such as at least 15 mg/ml, such as at least 20 mg/ml, such as at least 25 mg/ml.

In another embodiment of the invention the mutant strain of *Streptococcus thermophilus* is resistant to 2-deoxyglucose.

The term "resistant to 2-deoxyglucose" herein is defined by that a particular mutated bacterial strain has the ability to grow to a colony when streaked on a plate of M17 medium containing 20 mM 2-deoxyglucose after incubation at 40° C. for 20 hours. The presence of 2-deoxygluxcose in the culture medium will prevent the growth of non-mutated strains while the growth of the mutated strains is not affected or not affected significantly. Non-mutated strains which can be used as sensitive reference strains in the assessment of resistance preferably include the strains CHCC14994 and CHCC11976.

The mutant *Streptococcus thermophilus* strains of the invention excrete glucose into the milk when 9.5% B-milk is inoculated with $10^6$-$10^7$ CFU/ml of a *Streptococcus thermophilus* strain according to the invention and fermented with the *Streptococcus thermophilus* strains according to the invention at 40° C. for at least 20 hours. Preferably, such mutant strains alone will excrete at least 5 mg/ml glucose into B-milk when 9.5% B-milk is inoculated with $10^6$-$10^7$ CFU/ml of a *Streptococcus thermophilus* strain according to the invention and fermented with the *Streptococcus thermophilus* strains at 40° C. for at least 20 hours. The strains are still fully capable of acidifying milk although acidification time to pH 5 is delayed by 2-5 hours. The final fermented milk contains less than 15 mg/ml lactose in the fermented milk. The final fermented milk consequently has a higher inner sweetness index of approximately 2 fold or more.

In yet another embodiment, the mutant strain according to the invention can be characterized by its growth pattern. This is illustrated by the finding that the growth rate of the mutant strain is higher in M17 medium+2% galactose than in M17 medium+2% glucose. The growth rate is measured as the development in optical density of the exponentially growing culture at 600 nanometers ($OD_{600}$) with time.

In a preferred embodiment the growth rate is at least 5% higher, such as at least 10% higher, such as at least 15% higher, such as at least 20% higher, in M17 medium+2% galactose than in M17 medium+2% glucose.

Mutation in glcK Gene

In one preferred embodiment the mutation results in the replacement of the codon coding for glycine with the codon coding for arginine in position 249 in SEQ ID NO. 2. Preferably the mutation in the glcK gene results in the replacement of a G with a A in position 745 in SEQ ID NO. 1. Strain CHCC16731 has such a mutation.

In a preferred embodiment the mutation results in the replacement of the codon coding for serine with the codon coding for proline in position 72 in SEQ ID NO. 2 (not shown). Preferably the mutation in the glcK gene results in the replacement of a T with a C in position 214 in SEQ ID NO. 1 (not shown).

In another preferred embodiment the mutation results in the replacement of the codon coding for threonine with the codon coding for isoleucine in position 141 in SEQ ID NO. 2 (not shown).

Preferably, the mutation in the glcK gene results in the replacement of a C with a T on position 422 in SEQ ID NO. 1 (not shown).

It should be emphasized that the glcK gene of a *Streptococcus thermophilus* may be inactivated by other types of mutations in other sites of the glcK gene.

Mutation Reducing Transport of Glucose into the Cell

In a preferred embodiment the *Streptococcus thermophilus* strain carries a mutation that reduces the transport of glucose into the cell.

The term "a mutation that reduces the transport of glucose into the cell" as used herein refers to a mutation in a gene encoding a protein involved in transport of glucose which results in an accumulation of glucose in the environment of the cell.

The level of glucose in the culture medium of a *Streptococcus thermophilus* strain can readily be measured by methods known to the skilled person also when the culture medium is a milk substrate.

In preferred embodiments the mutation reduces the transport of glucose into the cell with at least 50%, such as at least 60%, such as at least 70%, such as at least 80%, such as at least 90%.

The transport of glucose into the cell can be determined by the glucose uptake assay as described by Cochu et al. (2003. Appl Environ Microbiol 69(9); 5423-5432).

Preferably, the *Streptococcus thermophilus* strain carries a mutation in a gene encoding a component of a glucose transporter, wherein the mutation inactivates the glucose transporter protein or has a negative effect on expression of the gene.

The component may be any component of a glucose transporter protein which is critical for the transport of glucose. It is e.g. contemplated that inactivation of any component of the glucose/mannose PTS in *Streptococcus thermophilus* depicted in FIG. 3 will result in inactivation of the glucose transporter function.

The term "the mutation inactivates the glucose transporter" as used herein refers to a mutation which results in an "inactivated glucose transporter", a glucose transporter protein which, if present in a cell, is not able to exert its normal function as well as mutations which prevent the formation of the glucose transporter protein or result in degradation of the glucose transporter protein.

In particular, an inactivated glucose transporter protein is a protein which compared to a functional glucose transporter protein is not able to facilitate transport of glucose over a plasma membrane or facilitates transport of glucose over a plasma membrane at a significantly reduced rate. The gene encoding such an inactivated glucose transporter protein compared to the gene encoding a functional glucose transporter protein comprises a mutation in the open reading frame (ORF) of the gene, wherein said mutation may include, but is not limited to, a deletion, a frameshift mutation, introduction of a stop codon or a mutation which results in an amino acid substitution, which changes the functional properties of the protein, or a promoter mutation that reduces or abolishes transcription or translation of the gene.

In preferred embodiments the mutation reduces the activity (the rate of transport of glucose) of the glucose transporter protein by at least 50%, such as at least 60%, such as at least 70%, such as at least 80%, such as at least 90%. The glucose transporter activity can be determined by the glucose uptake assay as described by Cochu et al. (2003. Appl Environ Microbiol 69(9); 5423-5432).

The term "functional glucose transporter protein" as used herein refers to a glucose transporter protein which, if present in a cell, facilitates transport of glucose over a plasma membrane.

In a preferred embodiment of the invention the *Streptococcus thermophilus* strain of the invention carries a mutation in the DNA sequence of the manN gene encoding the $IID^{Man}$ protein of the glucose/mannose phosphotransferase system, wherein the mutation inactivates the $IID^{Man}$ protein or has a negative effect on expression of the gene.

CHCC16731 has a threonine to proline change at position 79 in the manN gene encoding the $IID^{Man}$ protein of the glucose/mannose phosphotransferase system. Preferably the mutation in the ManN gene results in the replacement of an A with a C in position 235 in SEQ ID NO. 3.

Thus, in a preferred embodiment the *Streptococcus thermophilus* strain of the invention carries a mutation in the DNA sequence of the manN gene encoding the $IID^{Man}$ protein of the glucose/mannose phosphotransferase system, wherein the mutation results in the replacement of threonine to proline in position 79 of SEQ ID No. 4.

In another preferred embodiment of the invention the *Streptococcus thermophilus* strain of the invention carries a mutation in the DNA sequence of the manM gene encoding the $IIC^{Man}$ protein of the glucose/mannose phosphotransferase system, wherein the mutation inactivates the $IIC^{Man}$ protein or has a negative effect on expression of the gene.

In a specific preferred embodiment the mutation results in the replacement of the codon coding for glutamic acid with a stop codon in position 209 of SEQ ID NO. 6 of the $IIC^{Man}$ protein of the glucose/mannose phosphotransferase system (not shown). Preferably, the mutation results in the replacement of a G with a T in position 625 of SEQ ID NO. 5 (not shown).

Preferred *Streptococcus thermophilus* Strains of the Invention

In a preferred embodiment of the invention the *Streptococcus thermophilus* strain is selected from the group consisting of the *Streptococcus thermophilus* CHCC19216 strain that was deposited at Deutsche Sammlung von Mikroorganismen and Zellkulturen under accession No. DSM 32227 and a mutant strain derived therefrom, wherein the mutant strain is obtained by using one of the deposited strains as starting material, and wherein the mutant has retained or further improved the texturizing property and/or the glucose secreting property of said deposited strain.

In the present context, the term "mutant strain" should be understood as strains derived, or strains which can be derived from a strain (or their mother strain) of the invention by means of e.g. genetic engineering, radiation and/or chemical treatment. The "strains derived therefrom" can also be spontaneously occurring mutants. It is preferred that the "strains derived therefrom" are functionally equivalent mutants, e.g. mutants that have substantially the same, or improved properties as their mother strain. Especially, the term "mutant strains" refers to strains obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood as one mutagenization step followed by a screening/selection step), but it is presently preferred that no more than 20, or no more than 10, or no more than 5, treatments (or screening/selection steps) are carried out. In a presently preferred mutant less than 1%, less than 0.1%, less than 0.01%, less than 0.001% or even less than 0.0001% of the nucleotides in the bacterial genome have been replaced with another nucleotide, or deleted, compared to the mother strain.

Method of Obtaining a Sweetening *Streptococcus thermophilus* Strain

In a preferred embodiment of the invention the starting strain used for developing a sweetening *Streptococcus thermophilus* strain is a texturizing *Streptococcus thermophilus* strain, which may be obtained as described elsewhere in this specification.

In a preferred embodiment such a texturizing starting strain is selected from the group consisting of the *Streptococcus thermophilus* CHCC11342 strain that was deposited at Deutsche Sammlung von Mikroorganismen und Zellkulturen under accession No. DSM 22932, the *Streptococcus thermophilus* CHCC11976 strain that was deposited at Deutsche Sammlung von Mikroorganismen und Zellkulturen under accession No. DSM 22934, the *Streptococcus thermophilus* CHCC12339 strain that was deposited at Deutsche Sammlung von Mikroorganismen und Zellkulturen under accession No. DSM 24090, and strains derived therefrom.

Alternatively, the starting strain used for developing a sweetening *Streptococcus thermophilus* strain is a non-texturizing *Streptococcus thermophilus* strain, in which case the texturizing property is introduced into the sweetening *Streptococcus thermophilus* strain once produced, i.e. the sweetening strain is used as a starting strain in the method of obtaining a texturizing strain described elsewhere in this specification.

The first step of the method of a sweetening *Streptococcus thermophilus* strain is to provide a galactose positive strain, i.e. a strain that is capable of using galactose as a carbohydrate source. Galactose positive strains may be obtained by a method comprising the step of streaking the bacteria to be tested on agar plates, such as M17 agar plates containing a certain concentration, such as 2%, of galactose (sole carbohydrate source) and identifying colonies able to grow on the plates.

2-deoxyglucose and a determination of the growth pattern of the bacteria in M17 medium+2% galactose compared to in M17 medium+2% glucose is used for the selection of bacteria having a mutation in the glucokinase (glcK) gene.

One method for screening and isolating a strain of *Streptococcus thermophilus* with a mutated glcK gene comprises the following steps:

a) providing a galactose-fermenting *Streptococcus thermophilus* mother strain;

b) selecting and isolating from a pool of mutant *Streptococcus thermophilus* strains derived from the mother strain a pool of mutant *Streptococcus thermophilus* strains which are resistant to 2-deoxyglucose; and c) selecting and isolating from the pool of mutant *Streptococcus thermophilus* strains which are resistant to 2-deoxyglucose a mutant *Streptococcus thermophilus* strain if the growth rate of the mutant *Streptococcus thermophilus* strain is higher in M17 medium+2% galactose than in M17 medium+2% glucose.

The term "resistant to 2-deoxyglucose" herein is defined by that a particular mutated bacterial strain has the ability to grow to a colony when streaked on a plate of M17 medium containing 2% lactose or 2% galactose and containing 20 mM 2-deoxyglucose after incubation at 40° C. for 20 hours. The presence of 2-deoxygluxcose in the culture medium will prevent the growth of non-mutated strains while the growth of the mutated strains is not affected or not affected significantly. Non-mutated strains which can be used as sensitive reference strains in the assessment of resistance include the strain CHCC11976.

In an embodiment the method further comprises the step a1) subjecting the mother strain to mutagenization, such as subjecting the mother strain to a chemical and/or a physical mutagen.

In another embodiment the method further comprises a step d) selecting and isolating from a pool of 2-deoxyglucose resistant *Streptococcus thermophilus* strains derived from the *Streptococcus thermophilus* strain selected in step c) a *Streptococcus thermophilus* strain if the growth rate of the *Streptococcus thermophilus* strain is high in M17 medium+2% sucrose but zero or at least 0-50% reduced compared to the growth rate of the mother strain in M17 medium+2% glucose.

The galactose-fermenting *Streptococcus thermophilus* mother strains are capable of growth on/in M17 medium+2% galactose and are defined herein by that they have the ability to lower the pH in M17 broth containing 2% galactose as sole carbohydrate to 5.5 or lower when inoculated from an overnight culture at 1% and incubated for 24 hours at 37° C. Such galactose-positive strains have been described in WO2011/026863 (Chr. Hansen A/S) and WO2011/092300 (Chr. Hansen A/S).

In the present context, the term "strains derived therefrom" should be understood as strains derived, or strains which can be derived from texturizing or galactose-fermenting *Streptococcus thermophilus* mother strains by means of e.g. genetic engineering, radiation and/or chemical treatment. The "strains derived therefrom" can also be spontaneously occurring mutants. It is preferred that the "strains derived therefrom" are functionally equivalent mutants, e.g. mutants that have substantially the same, or improved properties (e.g. regarding texture or fermentation of galactose) as their mother strain. Especially, the term "strains derived therefrom" refers to strains obtained by subjecting a strain of the invention to any conventionally used mutagenization treatment including treatment with a chemical mutagen such as ethane methane sulphonate (EMS) or Nmethyl-N'-nitro-N-nitroguanidine (NTG), UV light, or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant less than 1%, less than 0.1%, less than 0.01%, less than 0.001% or even less than 0.0001% of the nucleotides in the bacterial genome have been replaced with another nucleotide, or deleted, compared to the mother strain.

In the present invention the expression "glcK gene encoding a glucokinase" means any DNA sequence of a *Streptococcus thermophilus* encoding a protein having glucokinase activity, including the specific glucokinase encoded by the DNA sequence of SEQ ID NO.: 1. A glucokinase catalyzes the reaction converting glucose to glucose-6-phosphate, cf. FIG. 1.

*Lactobacillus Delbrueckii* Subsp. *Bulgaricus* for Use in Combination with the *Streptococcus thermophilus* Strains of the Invention Glucose is used as a carbohydrate source by many lactic acid bacteria and any excreted glucose can be consumed by other microorganisms present in the fermented milk product.

To overcome this problem, the *Streptococcus thermophilus* strain of the present invention should preferably be used in combination with 2-deoxyglucose-resistant mutants of *Lactobacillus delbrueckii* subsp. *bulgaricus* which have either lost the ability to grow on glucose as carbohydrate source or exhibit an impaired ability to grow under such conditions. The mutant strains of *Lactobacillus delbrueckii* subsp. *bulgaricus* not only do not consume glucose secreted into the milk by other microorganisms that might be present, they also excrete high amounts of glucose into the surrounding medium and are, surprisingly, still fully capable of acidifying milk although acidification time to pH 5 is delayed by 2-5 hours. They are therefore as such useful in fermented milk applications.

Suitable 2-deoxyglucose-resistant mutants of *Lactobacillus delbrueckii* subsp. *bulgaricus* for use in combination with the *Streptococcus thermophilus* strain of the present invention are described in WO2013/160413. In a preferred embodiment of the invention, the strain is selected from the group consisting of the *Lactobacillus delbrueckii* subsp. *bulgaricus* strain CHCC16159 that was deposited at Deutsche Sammlung von Mikroorganismen und Zellkulturen under accession No. DSM 26420, the *Lactobacillus delbrueckii* subsp. *bulgaricus* strain CHCC16160 that was deposited at Deutsche Sammlung von Mikroorganismen und Zellkulturen under accession No. DSM 26421, and a mutant strain derived therefrom, wherein the mutant strain is obtained by using one of the deposited strains as starting material, and wherein the mutant has retained or further improved the lactose fermenting property and/or the glucose secreting property of said deposited strain.

Such food grade bacteria can be used to fortify fermented milk products with glucose. Glucose has a higher perceived sweetness than both lactose and galactose and as such the excretion of glucose to the milk substrate will result in a higher perceived (inner) sweetness in the fermented milk product.

The inventors of the present invention found that when a milk substrate is fermented with a *Streptococcus thermophilus* strain according to the invention and a 2-deoxyglucose-resistant mutant of *Lactobacillus delbrueckii* subsp. *bulgaricus* strain, the lactose level within the milk decreases significantly.

Lactose intolerance is a condition caused by the inability to digest lactose. Most lactose-intolerant individuals can tolerate some amount of lactose in their diet and the severity of their symptoms (including nausea, cramping, bloating, diarrhea, and flatulence) increases with the amount of lactose consumed.

Thus, it is of great importance in the industry to be able to produce food products which are either lactose-free or which have a reduced lactose content.

Composition

The present invention further relates to a composition comprising from $10^4$ to $10^{12}$ CFU (colony forming units)/g of a *Streptococcus thermophilus* strain according to the invention, such as from $10^5$ to $10^{11}$ CFU/g, such as from $10^6$ to $10^{10}$ CFU/g, or such as from $10^7$ to 109 CFU/g of the *Streptococcus thermophilus* strain.

In a preferred embodiment the *Streptococcus thermophilus* strain is unable to acidify 9.5% B-milk, defined as resulting in a pH decrease of less than 1.0 when 9.5% B-milk is inoculated with $10^6$-$10^7$ CFU/ml of the *Streptococcus thermophilus* strain and incubated for 14 hours at 40° C., and the composition further comprises an amount of a compound, which can trigger acidification of the 9.5% B-milk by the *Streptococcus thermophilus* strain CHCC16404 that was deposited at Deutsche Sammlung von Mikroorganismen and Zellkulturen under accession No. DSM 26722, defined as resulting in a pH decrease of 1.0 or more when 9.5% B-milk is inoculated with $10^6$-$10^7$ CFU/ml of the *Streptococcus thermophilus* strain and incubated for 14 hours at 40° C.

Preferably, the compound is sucrose.

Preferably, the amount of sucrose is from 0.000001% to 2%, such as from 0.00001% to 0.2%, such as from 0.0001% to 0.1%, such as from 0.001% to 0.05%.

In an especially preferred embodiment the composition further comprises from $10^4$ to $10^{12}$ CFU/g of a *Lactobacillus delbrueckii* subsp. *bulgaricus* strain, such as from $10^5$ to $10^{11}$ CFU/g, such as from $10^6$ to $10^{10}$ CFU/g, or such as from $10^7$ to $10^9$ CFU/g of the *Lactobacillus delbrueckii* subsp. *bulgaricus* strain.

A preferred composition of the present invention comprises, for example, *Lactobacillus delbrueckii* subsp. *bulgaricus* strain CHCC16159 and/or *Lactobacillus delbrueckii* subsp. *bulgaricus* strain CHCC16160 in combination with *Streptococcus thermophilus* strain CHCC16731. A further preferred composition comprises *Lactobacillus delbrueckii* subsp. *bulgaricus* strain CHCC16159 and/or *Lactobacillus delbrueckii* subsp. *bulgaricus* CHCC16160 in combination with *Streptococcus thermophilus* strain CHCC19216.

*Lactobacillus delbrueckii* subsp. *bulgaricus, Streptococcus thermophilus* and other lactic acid bacteria are commonly used as starter cultures serving a technological purpose in the production of various foods, such as in the dairy industry, such as for fermented milk products. Thus, in another preferred embodiment the composition is suitable as a starter culture.

Starter cultures may be provided as frozen or dried starter cultures in addition to liquid starter cultures. Thus, in yet another preferred embodiment the composition is in frozen, freeze-dried or liquid form.

As disclosed in WO 2005/003327, it is beneficial to add certain cryoprotective agents to a starter culture. Thus, a starter culture composition according to the present invention may comprise one or more cryoprotective agent(s) selected from the group consisting of inosine-5'-monophosphate (IMP), adenosine-5'-monophosphate (AMP), guanosine-5'-monophosphate (GMP), uranosine-5'-monophosphate (UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any such compounds.

Method of Producing a Fermented Milk Product

The invention is further directed to a method of producing a fermented milk product comprising inoculating and fermenting a milk substrate with at least one *Streptococcus thermophilus* strain according to the present invention.

The term "milk" is to be understood as the lacteal secretion obtained by milking any mammal, such as a cow, a sheep, a goat, a buffalo or a camel. In a preferred embodiment, the milk is cow's milk.

The term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder.

Preferably, at least part of the protein in the milk substrate is proteins naturally occurring in milk, such as casein or whey protein. However, part of the protein may be proteins which are not naturally occurring in milk.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the action of a microorganism. Preferably, fermentation in the methods of the invention comprises conversion of lactose to lactic acid.

Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid or liquid form (fermented milk product).

The term "fermented milk product" as used herein refers to a food or feed product wherein the preparation of the food or feed product involves fermentation of a milk substrate with a lactic acid bacteria. "Fermented milk product" as used herein includes but is not limited to products such as yoghurt, cheese, sour cream and buttermilk as well as fermented whey.

In a preferred embodiment the concentration of *Streptococcus thermophilus* cells inoculated is from $10^4$ to $10^9$ CFU *Streptococcus thermophilus* cells per ml of milk substrate, such as from $10^4$ CFU to $10^8$ CFU *Streptococcus thermophilus* cells per ml of milk substrate.

In another preferred embodiment of the method of the invention the *Streptococcus thermophilus* strain is unable to acidify the 9.5% B-milk, defined as resulting in a pH decrease of less than 1.0 when 9.5% B-milk is inoculated with $10^6$-$10^7$ CFU/ml of the *Streptococcus thermophilus* strain and incubated for 14 hours at 40° C., and the milk substrate is added an amount of a compound, effective to trigger acidification of 9.5% B-milk by the *Streptococcus thermophilus* strain, defined as resulting in a pH decrease of 1.0 or more when 9.5% B-milk is inoculated with $10^6$-$10^7$ CFU/ml of the *Streptococcus thermophilus* strain and incubated for 14 hours at 40° C.

Preferably, the compound is sucrose.

Preferably, the amount of sucrose is from 0.000001% to 2%, such as from 0.00001% to 0.2%, such as from 0.0001% to 0.1%, such as from 0.001% to 0.05%.

In a preferred embodiment the method for producing the fermented milk product comprises inoculating and fermenting a milk substrate with at least one *Streptococcus thermophilus* strain according to any one of claims 1 to 16 and at least one *Lactobacillus delbrueckii* subsp. *bulgaricus* strain, preferably a 2-deoxyglucose-resistant mutant of a *Lactobacillus delbrueckii* subsp. *bulgaricus* strain.

In another preferred embodiment the fermented milk product is a yoghurt or a cheese.

Examples of cheeses which are prepared by fermentation with *Streptococcus thermophilus* and *Lactobacillus delbrueckii* subsp. *bulgaricus* include Mozzarella and pizza cheese (Høier et al. (2010) in The Technology of Cheesemaking, 2$^{nd}$ Ed. Blackwell Publishing, Oxford; 166-192).

Preferably the fermented milk product is a yoghurt.

In the present context, a yoghurt starter culture is a bacterial culture which comprises at least one *Lactobacillus delbrueckii* subsp. *bulgaricus* strain and at least one *Streptococcus thermophilus* strain. In accordance herewith, the term "yoghurt" refers to a fermented milk product obtainable by inoculating and fermenting milk with a composition comprising a *Lactobacillus delbrueckii* subsp. *bulgaricus* strain and a *Streptococcus thermophilus* strain.

Fermented Milk Product

The present invention further relates to a fermented milk product comprising at least one *Streptococcus thermophilus* strain according to the invention.

In a preferred embodiment the fermented milk product comprises at least one *Streptococcus thermophilus* strain according to the invention and at least one *Lactobacillus delbrueckii* subsp. *bulgaricus* strain, preferably at least one 2-deoxyglucose-resistant mutant of a *Lactobacillus delbrueckii* subsp. *bulgaricus* strain.

In another preferred embodiment the fermented milk product is a yoghurt or a cheese. Preferably, the fermented milk product is a yoghurt.

Use of the *Streptococcus thermophilus* strain of the invention

A further aspect of the invention relates to the use of a *Streptococcus thermophilus* strain according to the invention for the preparation of a fermented milk product.

A further aspect of the invention relates to the use of a *Streptococcus thermophilus* strain according to the invention for increasing the sweetness of a fermented milk product.

A further aspect of the invention relates to the use of a *Streptococcus thermophilus* strain according to the invention for increasing the texture in a fermented milk product.

A further aspect of the invention relates to the use of a *Streptococcus thermophilus* strain according to the invention for increasing both the sweetness and the texture in a fermented milk product.

A further aspect of the invention relates to the use for increasing texture, wherein the said strain generates a texture in fermented milk greater than about 40 Pa measured as shear stress after 12 hours of growth at 37 degrees C.

A further aspect of the invention relates to the use of a *Streptococcus thermophilus* strain according to the invention in combination with a *Lactobacillus delbrueckii* subsp. *bulgaricus* strain for the preparation of a fermented milk product.

A further aspect of the invention relates to the use of a *Streptococcus thermophilus* strain according to the invention in combination with a *Lactobacillus delbrueckii* subsp. *bulgaricus* strain for increasing the sweetness of a fermented milk product.

A further aspect of the invention relates to the use of a *Streptococcus thermophilus* strain according to the invention in combination with a *Lactobacillus delbrueckii* subsp. *bulgaricus* strain for increasing the texture in a fermented milk product.

A further aspect of the invention relates to the use of a *Streptococcus thermophilus* strain according to the invention in combination with a *Lactobacillus delbrueckii* subsp. *bulgaricus* strain for increasing both sweetness and the texture in a fermented milk product.

A further aspect of the invention relates to the use for increasing the texture, wherein the said strain generates a texture in fermented milk greater than about 40 Pa measured as shear stress after 12 hours of growth at 37 degrees C.

A further aspect of the invention relates to the uses comprising a *Lactobacillus delbrueckii* subsp. *bulgaricus* strain, wherein the *Lactobacillus delbrueckii* subsp. *bulgaricus* strain is a 2-deoxyglucose resistant strain.

A further aspect of the present invention relates to a fermented milk product according to the invention for use in reducing the calorie intake.

The fermented milk product according to the invention is thought to be especially useful in the diet of persons suffering from overweight or obesity.

Thus, in a preferred embodiment the fermented milk product according to the invention is for use in reducing the calorie intake of a person suffering from overweight or obesity.

Overweight and obesity are medical conditions defined by the World Health Organization (WHO) as abnormal or excessive fat accumulation that presents a risk to health. The Body Mass Index (BMI) can be used as a rough guide to classify overweight and obesity in adults and is calculated as a person's weight in kilograms divided by the square of his/her height in meters ($kg/m^2$). The WHO definition states that a BMI greater than or equal to 25 is overweight and that a BMI greater than or equal to 30 is obesity.

A further aspect of the present invention relates to the use of a *Streptococcus thermophilus* strain according to the invention for decreasing the lactose content in a fermented milk product.

A further aspect of the present invention is directed to a fermented milk product according to the invention for use in avoiding symptoms of lactose intolerance.

A further aspect relates to a composition of the invention for use as a medicament.

Embodiments of the present invention are described below, by way of non-limiting examples.

SEQUENCE LISTING

SEQ ID NO. 1 shows the DNA sequence of the mutated glucokinase gene of strain CHCC16731.

SEQ ID NO. 2 shows the amino acid sequence encoded by SEQ ID NO. 1.

SEQ ID NO. 3 shows the DNA sequence of the mutated ManN gene of strain CHCC16731.

SEQ ID NO. 4 shows the amino acid sequence encoded by SEQ ID NO. 3.

SEQ ID NO. 5 shows the DNA sequence of the ManM gene (not mutated) of strain CHCC16731.

SEQ ID NO. 6 shows the amino acid sequence encoded by SEQ ID NO. 5.

LIST OF ASPECTS AND EMBODIMENTS OF THE INVENTION

1. A *Streptococcus thermophilus* strain, wherein the strain is galactose-fermenting, wherein the strain carries a mutation in the DNA sequence of the glcK gene encoding a glucokinase protein, wherein the mutation inactivates the glucokinase protein or has a negative effect on expression of the gene, and wherein the strain carries a mutation in the promoter region of the GalK gene encoding a galactokinase protein, with the proviso that the strain is not the *Streptococcus thermophilus* strain CHCC16731 that was deposited at Deutsche Sammlung von Mikroorganismen and Zellkulturen under accession No. DSM 28889.

2 The *Streptococcus thermophilus* strain according to item 1, wherein the strain is 2-deoxyglucose resistant.

3. The *Streptococcus thermophilus* strain according to item 1 or 2, wherein the strain carries a mutation that reduces the transport of glucose into the cell.

4. The *Streptococcus thermophilus* strain according to item 3, wherein the strain carries a mutation in a gene encoding a component of a glucose transporter, wherein the mutation inactivates the glucose transporter or has a negative effect on expression of the gene.

5. The *Streptococcus thermophilus* strain according to item 4, wherein the strain of the invention carries a mutation in the DNA sequence of the manN gene encoding the $IID^{Man}$ protein of the glucose/mannose phosphotransferase system, wherein the mutation inactivates the $IID^{Man}$ protein or has a negative effect on expression of the gene.

6. The *Streptococcus thermophilus* strain according to any of the preceding items, wherein the strain increases the amount of glucose in 9.5% B-milk to at least 5 mg/ml when inoculated into the 9.5% B-milk at a concentration of $10^6$-$10^7$ CFU/ml and grown at 40° C. for 20 hours.

7. The *Streptococcus thermophilus* strain according to any of the preceding items, wherein the strain increases the amount of glucose in 9.5% B-milk with 0.05% sucrose to at least 5 mg/ml when inoculated into the 9.5% B-milk with 0.05% sucrose at a concentration of $10^6$-$10^7$ CFU/ml and grown at 40° C. for 20 hours.

8. The *Streptococcus thermophilus* strain according to any of the preceding items, wherein the strain carries a mutation in the promoter region of the GalK gene downstream of the −10 promoter box (Pribnow box).

9. The *Streptococcus thermophilus* strain according to item 8, wherein the mutation in the promoter region of the GalK gene is a mutation in the position 3 nucleotides downstream of the −10 promoter box.

10. The *Streptococcus thermophilus* strain according to item 9, wherein the mutation in the promoter region of the GalK gene is a mutation of C in the position 3 nucleotides downstream of the −10 promoter box into A.

11. The *Streptococcus thermophilus* strain according to any of the preceding items, wherein the mutation in the promoter region of the GalK gene is a mutation in the −10 promoter box.

12. The *Streptococcus thermophilus* strain according to item 11, wherein the C of the −10 promoter box is replaced with a nucleotide selected from the group consisting of A, G and T.

13. The *Streptococcus thermophilus* strain according to item 12, wherein the C of the −10 promoter box is replaced with a nucleotide selected from the group consisting of A and T.

14. The *Streptococcus thermophilus* strain according to item 13, wherein the C of the −10 promoter box is replaced with T.

15. The *Streptococcus thermophilus* strain according to any of the preceding items, wherein the strain generates a texture in fermented milk greater than about 40 Pa measured as shear stress after 12 hours of growth at 37 degrees C.

16. A *Streptococcus thermophilus* strain, wherein the strain is selected from the group consisting of the *Streptococcus thermophilus* CHCC19216 strain that was deposited at Deutsche Sammlung von Mikroorganismen and Zellkulturen under accession No. DSM 32227, and a mutant strain derived therefrom, wherein the mutant strain is obtained by using one of the deposited strains as starting material, and wherein the mutant has retained or further improved the texturizing property and the glucose secreting property of said deposited strain.

17. A composition comprising from $10^4$ to $10^{12}$ CFU/g of a *Streptococcus thermophilus* strain according to any of items 1 to 16.

18. The composition of item 17, wherein the *Streptococcus thermophilus* strain is unable to acidify the 9.5% B-milk, defined as resulting in a pH decrease of less than 1.0 when 9.5% B-milk is inoculated with $10^6$-$10^7$ CFU/ml of the *Streptococcus thermophilus* strain and incubated for 14 hours at 40° C., and wherein the composition further comprises an amount of sucrose effective to trigger acidification of the 9.5% B-milk, defined as resulting in a pH decrease of 1.0 or more when 9.5% B-milk is inoculated with $10^6$-$10^7$ CFU/ml of the *Streptococcus thermophilus* strain and incubated for 14 hours at 40° C.

19. The composition of items 17 or 18 further comprising from $10^4$ to $10^{12}$ CFU/g of a 2-deoxyglucose-resistant mutant of *Lactobacillus delbrueckii* subsp. *bulgaricus* strain.

20. A method for producing a fermented milk product comprising inoculating and fermenting a milk substrate with at least one *Streptococcus thermophilus* strain according to any one of items 1 to 16.

21. A method according to item 20, wherein the *Streptococcus thermophilus* strain is unable to acidify 9.5% B-milk, defined as resulting in a pH decrease of less than 1.0 when 9.5% B-milk is inoculated with $10^6$-$10^7$ CFU/ml of the *Streptococcus thermophilus* strain and incubated for 14 hours at 40° C., and wherein the milk substrate is added an amount of sucrose effective of triggering acidification of the B-milk, defined as resulting in a pH decrease of 1.0 or more when 9.5% B-milk is inoculated with $10^6$-$10^7$ CFU/ml of the *Streptococcus thermophilus* strain and incubated for 14 hours at 40° C.

22. A method according to any one of items 20 to 21 comprising inoculating and fermenting a milk substrate with at least one *Streptococcus thermophilus* strain according to any one of claims 1 to 16 and at least one 2-deoxyglucose-resistant mutant of a *Lactobacillus delbrueckii* subsp. *bulgaricus* strain.

23. A fermented milk product comprising at least one *Streptococcus thermophilus* strain according to any one of items 1 to 16.

24. A fermented milk product according to item 23 comprising at least one *Streptococcus thermophilus* strain according to any one of claims 1 to 15 and at least one 2-deoxyglucose-resistant mutant of a *Lactobacillus delbrueckii* subsp. *bulgaricus* strain.

25. Use of a *Streptococcus thermophilus* strain according to any one of items 1 to 16 for the preparation of a fermented milk product.

26. Use of a *Streptococcus thermophilus* strain according to any one of items 1 to 16 for increasing the sweetness of a fermented milk product.

27. Use of a *Streptococcus thermophilus* strain according to any one of items 1 to 16 for increasing the texture in a fermented milk product.

28. Use of a *Streptococcus thermophilus* strain according to any one of items 1 to 16 for increasing both the sweetness and the texture in a fermented milk product.

29. Use according to any of items 27-28, wherein the said strain generates a texture in fermented milk greater than about 40 Pa measured as shear stress after 12 hours of growth at 37 degrees C.

30. Use of a *Streptococcus thermophilus* strain according to any one of items 1 to 16 in combination with a *Lactobacillus delbrueckii* subsp. *bulgaricus* strain for the preparation of a fermented milk product.

31. Use of a *Streptococcus thermophilus* strain according to any one of items 1 to 16 in combination with a *Lactobacillus delbrueckii* subsp. *bulgaricus* strain for increasing the sweetness of a fermented milk product.

32. Use of a *Streptococcus thermophilus* strain according to any one of items 1 to 16 in combination with a *Lactobacillus delbrueckii* subsp. *bulgaricus* strain for increasing the texture in a fermented milk product.

33. Use of a *Streptococcus thermophilus* strain according to any one of items 1 to 16 in combination with a *Lactobacillus delbrueckii* subsp. *bulgaricus* strain for increasing both sweetness and the texture in a fermented milk product.

34. Use according to any of items 32-33, wherein the said strain generates a texture in fermented milk greater than about 40 Pa measured as shear stress after 12 hours of growth at 37 degrees C.

Use according to any of items 30-34, wherein the *Lactobacillus delbrueckii* subsp. *bulgaricus* strain is a 2-deoxyglucose resistant strain.

36. A fermented milk product according to any one of items 23 to 24 for use in avoiding symptoms of lactose intolerance.

EXAMPLES

Materials and Methods

Medium:

For *Streptococcus thermophilus*, the medium used is the M17 medium known to persons skilled in the art.

The M17 agar medium has the following composition per liter $H_2O$:

agar, 12.75 g
ascorbic acid, 0.5 g
casein peptone (tryptic), 2.5 g
disodium β-glycerophosphate pentahydrate, 19 g
magnesium sulfate hydrate, 0.25 g
meat extract, 5 g
meat peptone (peptic), 2.5 g
soyapeptone (papainic), 5 g
yeast extract, 2.5 g
final pH 7.1±0.2 (25° C.)

and M17 broth has the following composition per liter $H_2O$:

ascorbic acid, 0.5 g
magnesium sulfate, 0.25 g
meat extract, 5 g
meat peptone (peptic), 2.5 g
sodium glycerophosphate, 19 g
soya peptone (papainic), 5 g
tryptone, 2.5 g
yeast extract, 2.5 g
final pH 7.0±0.2 (25° C.)

Carbon sources added are sterile lactose 20 g/l, glucose 20 g/l or galactose 20 g/l.

As known to the skilled person, the M17 medium is a medium that is considered to be suitable for growth of *Streptococcus thermophilus*. Further, as understood by the skilled person, in the present context, a M17 concentrate may be supplied from different suppliers and independently of the specific supplier one will (within standard measurement uncertainty) get the same herein relevant result of 2-deoxyglucose resistance for a herein relevant cell of interest.

The medium used for culturing *Lactobacillus delbrueckii* subsp. *bulgaricus* was MRS-IM medium. MRS-IM was used either in the form of agar plates or broth.

The MRS-IM agar medium had the following composition per liter $H_2O$:

| | | |
|---|---|---|
| Tryptone | Oxoid L 42 | 10.0 g |
| Yeast extract | Oxoid L 21 | 5.0 g |
| Tween 80 | Merck nr 8.22187 | 1.0 g |
| $K_2HPO_4$ | Merck nr 105104 | 2.6 g |
| Na-acetate | Merck nr 106267 | 5.0 g |
| Diammonium-hydrogen-citrate | Merck nr 101154 | 2.0 g |
| $MgSO_4$, 7 H2O | Merck nr 105882 | 0.2 g |
| $MnSO_4$, H2O | Merck nr 105941 | 0.05 g |
| Agar | SO-BI-GEL | 13.0 g |

The pH was adjusted after autoclaving to 6.9±0.1 at 25° C.

The MRS-IM broth used in the below examples for liquid cultures had the following composition per liter $H_2O$:

| | | |
|---|---|---|
| Tryptone | Oxoid L 42 | 10.0 g |
| Yeast extract | Oxoid L 21 | 5.0 g |
| Tween 80 | Merck nr 8.22187 | 1.0 g |
| $K_2HPO_4$ | Merck nr 105104 | 2.6 g |
| Na-acetate | Merck nr 106267 | 5.0 g |
| Diammonium-hydrogen-citrate | Merck nr 101154 | 2.0 g |
| $MgSO_4$, 7 H2O | Merck nr 105882 | 0.2 g |
| $MnSO_4$, H2O | Merck nr 105941 | 0.05 g |

The pH is adjusted after autoclaving to 6.9±0.1 at 25° C. The carbon sources, lactose 20 g/l or glucose 20 g/l, were first filtered sterile and then added to the autoclaved broth.

The above MRS-IM media can be varied to some extent without affecting the capability of the media to support growth of *Lactobacillus delbrueckii* subsp. *bulgaricus*. Further, as will be understood by the skilled person, a MRS-IM concentrate or the various components described above may be obtained from different suppliers and used for the preparation of a MRS-IM medium. These media will likewise be used in the below examples, in particular in the 2-deoxyglucose resistance selection assay.

Mother Strains

*Streptococcus thermophilus* CHCC11976 (galactose-fermenting strain with a mutation in the GalK gene as described in WO 2011/026863).

*Streptococcus thermophilus* CHCC12339 (phage resistant and texturizing as described in WO2011/092300).

*Streptococcus thermophilus* CHCC18948 (galactose-fermenting mutant of CGCC12339 with a mutation in the GalK gene)

2-Deoxy-Glucose Resistant Strains

*Streptococcus thermophilus* CHCC16165 (2-deoxyglucose resistant mutant of CHCC11976).

*Streptococcus thermophilus* CHCC16731 (sweetening and texturizing mutant of CHCC16165).

*Streptococcus thermophilus* CHCC19216 (sweetening and texturizing mutant of CHCC18948).

Example 1: Use of 2-Deoxyglucose to Isolate Glucose Kinase Mutant of *Streptococcus thermophilus* CHCC11976 with Enhanced Excretion of Glucose In order to isolate mutants of *Streptococcus thermophilus* strain CHCC11976, cells derived from the growth of a single colony were inoculated into 10 ml of M17 broth containing 2% lactose and grown overnight at 40° C.

Next day, the strains were plated in serial dilutions on M17 agar plates containing 2% galactose and a concentration of 2-deoxyglucose of 20 mM (CHCC11976) and incubated for 20 hours at 40° C. Resistant colonies were at first re-streaked on the same type of agar plates as they were selected. Survivors were used to inoculate fresh M17 broth containing either 2% lactose, 2% galactose or 2% glucose and growth was measured.

From this, a number of mutants that were able to grow faster on galactose than on glucose were identified as outlined in Example 2. One such mutant was CHCC16165.

Example 2: 2-Deoxyglucose Resistance Mutant Growth Pattern

To ensure the selection of 2-deoxyglucose resistant mutants that can grow on galactose, two strains that were selected from a galactose-fermenting strain collection were used. While these galactose-fermenting strains still grow at least 10% faster in exponential phase in M17 broth+2% glucose than in M17 broth+2% galactose, the 2-deoxyglucose resistant mutant derivative of CHCC11976, i.a. CHCC16165, on the other hand, are characterized by growing faster in exponential phase in M17 broth+2% galactose than in M17 broth+2% glucose.

Growth in exponential phase is herein measured as the development in optical density of the exponentially growing culture at 600 nanometers ($OD_{600}$) with time at 40° C.

As known by the skilled person, it may vary from species to species when the culture is in exponential growth. The skilled person will know how to determine the growth in exponential phase, e.g. between $OD_{600}$ 0.1-1.0.

The optical density (OD) of the culture is measured in a spectrophotometer.

Conclusion:

Based on the 2-deoxyglucose resistance mutant growth pattern of this Example 2—for a specific strain of interest (e.g. one from a relevant commercial product)—the skilled person can routinely test if this specific strain of interest has the herein relevant growth pattern which is a property of the selected mutants.

Example 3: Selection of a Hyper-Lactose Fermenting and Glucose Secreting Mutant of *Streptococcus thermophilus* CHCC16165

In order to isolate a hyper-lactose fermenting and glucose secreting mutant of *Streptococcus thermophilus* strain CHCC16165, cells derived from the growth of a single colony were inoculated into 10 ml of M17 broth containing 2% galactose and grown overnight at 40° C.

Next day, the strain was plated in serial dilutions on M17 agar plates containing 2% sucrose and a concentration of 2-deoxyglucose of 40 mM and incubated for 20 hours at 40° C. 10 random colonies were picked from the plate and used to inoculate fresh M17 broth containing 2% sucrose and incubated over night at 40° C. The CHCC16165 mutants were transferred to fresh M17 media containing 2% sucrose.

Example 4. Carbohydrate Analysis of Fermented Milk

The mutants obtained in Example 3 and strain CHCC16165 were grown in 9.6% B-milk containing 0.01% sucrose. After acidification, the milk acidified with CHCC16165 had a lactose concentration of 14.9, a galactose concentration of 8.4 and a glucose concentration of 5.7. In comparison the milk acidified with the best performing mutant of CHCC16165 had a lactose concentration of 9.3, a galactose concentration of 10.5 and a glucose concentration of 9.9. The said best mutant of CHCC16165 was designated CHCC16731 and it was subjected to further testing in fermentation of milk when used in combination with *Lactobacillus delbrueckii* subsp. *bulgaricus* strains CHCC16159 and CHCC16160 (described in WO2013/160413).

Overnight cultures of CHCC16165 and CHCC16731 in combination with each of CHCC16159 and CHCC16160 were added to 200 ml samples of B-milk and acidified at 40° C.

The results were as listed in Table 1:

| Strain blend | Lactose mg/ml | Galactose mg/ml | Glucose mg/ml |
|---|---|---|---|
| CHCC16165 + CHCC16159 | 14.0 | 10.9 | 6.5 |
| CHCC16165 + CHCC16160 | 13.5 | 11.0 | 6.9 |
| CHCC16731 + CHCC16159 | 1.0 | 22.0 | 16.2 |
| CHCC16731 + CHCC16160 | 1.0 | 22.5 | 16.0 |
| B-milk | 48.9 | Not detectable | Not detectable |

As will appear from the results of Table 1, CHCC16731 is capable of removing almost all of the lactose from the milk. Also, CHCC16731 produces and secretes high levels of both galactose and glucose into the milk. Taking into account that sucrose is a 100 reference, and the sweetness of lactose is 16, the sweetness of galactose is 32 and the sweetness of glucose is 74.3, the fermented milk product produced with CHCC16731 has a highly increased sweetness.

Example 5. Production of a Galactose Positive Mutant of *Streptococcus thermophilus* CHCC12339

The *Streptococcus thermophilus* CHCC12339 was grown overnight in M17 containing 2% lactose at 40° C. An overnight culture was plated (100 µl) on a M17 plate containing 2% galactose and incubated at 40° C. anaerobically. 22 colonies appear on the M17 containing 2% galactose plates. 16 of these are re-streaked on the same type of plates, and 8 of these are transferred to liquid M17 containing 2% galactose, all of which result in growth, and 4 of these cultures are frozen. 2 of the frozen cultures are spread on M17 plates containing 2% galactose and 40 mM 2-deoxyglucose, and for each culture 8 of the resulting colonies were selected. The 16 2-deoxyglucose mutants were transferred to liquid M17 containing 2% lactose and 2% galactose and grown overnight at 40° C., after which the mutants were grown in liquid M17 containing 2% galactose for 3 nights and the production of galactose and glucose was measured and followed through the growth. Based on the production of galactose and glucose 7 cultures were selected for milk acidification testing by adding 2 ml culture to 200 ml 9.5% B-milk containing 0.05% sucrose. 3 mutants have acidification profiles resembling that of the mother strain CHCC12339, and those 3 mutants are streaked to single colonies and incubated for 48 hours. Subsequently, the colonies are transferred to liquid M17 containing 2% galactose and the growth for the 3 mutants is tested against CH12339. The mutant having the highest growth is selected and purified once more by streaking to single colony 3 times to produce a purified galactose positive strain named CHCC18948 (galactose positive variant of CHCC12339).

Example 6. Production of a 2-Deoxyglucose Mutant of *Streptococcus thermophilus* CHCC18948 with Enhanced Excretion of Glucose 100 μl of the CHCC18949 culture is spread on M17 plates containing 2% galactose and 20 mM or 40 mM 2-deoxyglucose and incubated overnight at 40° C. 8 colonies from the 20 mM plates and 8 colonies from the 40 mM plates are selected and grown in liquid M17 containing 2% galactose and 20 mM 2-oxyglucose. The resulting cultures are frozen and re-streaked, and 12 of the resulting colonies are started in M17 medium and used to acidify B-milk. 1% of an overnight culture of the 2-deoxyglucose mutant is inoculated into 200 ml 9.5% B-milk containing 0.05% sucrose and acidified at 40° C. All 12 2-deoxyglucose mutants of CHCC18948 produced fermented mill products with low concentrations of lactose and high concentrations of galactose and glucose. 7 mutants were selected for retesting alone and for testing together with *Lactobacillus delbrueckii* subsp. *bulgaricus* strains CHCC16159 (described in WO2013/160413). Again 1% of an overnight culture of the 2-deoxyglucose mutant is inoculated into 200 ml 9.5% B-milk containing 0.05% sucrose and acidified at 40° C.

The results are given in Table 2:

| Strain/strain blend | Lactose mg/ml | Galactose mg/ml | Glucose mg/ml |
|---|---|---|---|
| CHCH18948-Mutant1 | Not detectable | 17.9 | 20.8 |
| CHCH18948-Mutant2 | Not detectable | 18.9 | 23.8 |
| CHCH18948-Mutant3 | 9.5 | 13.6 | 14.5 |
| CHCH18948-Mutant7 | Not detectable | 19.1 | 24.2 |
| CHCH18948-Mutant10 | 1.7 | 16.0 | 21.1 |
| CHCH18948-Mutant11 | Not detectable | 17.5 | 22.9 |
| CHCH18948-Mutant12 | 3.6 | 16.9 | 18.7 |
| CHCH18948-Mutant1 + CHCC16159 | 7.9 | 16.7 | 9.6 |
| CHCH18948-Mutant2 + CHCC16159 | 9.1 | 18.4 | 10.3 |
| CHCH18948-Mutant3 + CHCC16159 | 3.5 | 18.6 | 11.9 |
| CHCH18948-Mutant7 + CHCC16159 | 10.7 | 15.1 | 7.7 |
| CHCH18948-Mutant10 + CHCC16159 | 10.2 | 16.2 | 8.5 |
| CHCH18948-Mutant12 + CHCC16159 | 10.5 | 15.9 | 8.4 |
| CHCH18948-Mutant12 + CHCC16159 | 3.3 | 19.0 | 10.9 |
| B-milk | 47.1 | Not detectable | Not detectable |

The three best mutants are mutants 2, 3 and 12, and they are re-tested in B-milk containing 0.05% sucrose alone and in combination with *Lactobacillus delbrueckii* subsp. *bulgaricus* strains CHCC16159, CHCC16160 and CHCC16161 (described in WO2013/160413)

The results are given in Table 3:

| Strain/strain blend | Lactose mg/ml | Galactose mg/ml | Glucose mg/ml |
|---|---|---|---|
| CHCH16159 | 9.9 | 14.8 | 8.7 |
| CHCH16160 | 1.6 | 18.5 | 17.5 |
| CHCH16161 | 12.8 | 13.7 | 8.6 |
| CHCH18948-Mutant2 + CHCH16159 | 6.8 | 19.4 | 12.0 |
| CHCH18948-Mutant2 + CHCH16160 | Not detectable | 21.3 | 17.6 |
| CHCH18948-Mutant2 + CHCH16161 | Not detectable | 20.5 | 17.1 |
| CHCH18948-Mutant12 + CHCH16159 | 5.0 | 19.3 | 12.1 |
| CHCH18948-Mutant12 + CHCC16160 | 1.4 | 21.8 | 16.5 |
| CHCH18948-Mutant12 + CHCC16161 | 4.2 | 20.2 | 14.6 |
| CHCH18948-Mutant3 + CHCC16159 | 1.6 | 19.8 | 13.2 |
| CHCH18948-Mutant3 + CHCC16160 | Not detectable | 20.2 | 16.5 |
| CHCH18948-Mutant3 + CHCC16161 | 3.0 | 19.5 | 16.5 |
| CHCH18948-Mutant2 | Not detectable | 19.7 | 27.3 |
| CHCH18948-Mutant3 | Not detectable | 19.9 | 27.1 |
| CHCH18948-Mutant12 | 4.7 | 15.1 | 17.0 |
| B-milk | 42.8 | Not detectable | Not detectable |

Based on the above data CHCH18948-Mutant3 was selected as the best mutant and it was designated CHCC19216. As will appear from the above data CHCC19216 is capable of removing almost all of the lactose from the milk. Also, CHCC19216 produces and secretes high levels of both galactose and glucose into the milk. Taking into account that sucrose is a 100 reference, and the sweetness of lactose is 16, the sweetness of galactose is 32 and the sweetness of glucose is 74.3, the fermented milk product produced with CHCC19216 has a highly increased sweetness.

Example 7. Texturizing Property of CHCC16731 and CHCC19216

The texturizing property of strains CHCC16731 and CHCC19216 were tested by measurement of the shear stress by use of the following assay:

Seven days after incubation, the fermented milk was brought to 13° C. and stirred gently by means of a stick fitted with a bored disc until homogeneity of the sample. The rheological properties of the sample were assessed on a rheometer (Anton Paar Physica ASC/DSR301 Rheometer (Autosampler), Anton Paar® GmbH, Austria) using the following settings:

Wait time (to rebuild to somewhat original structure)

5 minutes without oscillation or rotation

Oscillation (to measure G' and G" for calculation of G*)

$\gamma$=0.3%, frequency (f)=[0.5 . . . 8] Hz 6 measuring points over 60 s (one every 10 s)

Rotation (to measure shear stress at 300 1/s etc.)

$\dot{\gamma}$=[0.2707-300] 1/s and $\dot{\gamma}$=[275-0.2707] 1/s 21 measuring point over 210 s (one every 10 s) going up to 300 1/s and 21 measuring points over 210 s (one every 10 s) going down to 0.2707 1/s For further analysis the shear stress at 300 1/s was chosen.

The strains CHCC16731 and CHCC19216 in the blends listed in Table 4 were used to acidify samples of 200 ml 9.5% B-milk using an inoculum of 0.024% until the pH reached 4.55.

The results are given in Table 4:

| Blend No. | Content of St of invention | Content of St CHCC16404 | Content of St CHCC15757 | Content of Lb CHCC-16159 | Shear stress Pa |
|---|---|---|---|---|---|
| 1 | 72.73% CHCC16731 | 13.64% | 4.54% | 9.09% | 41.3 |
| 2 | 72.73% CHCC19216 | 13.64% | 4.54% | 9.09% | 51.5 |
| 3 | 36.36% CHCC16731 + 33.36% CHCC19216 | 13.64% | 4.54% | 9.09% | 43.3 |

Lb: *L. delbruecki* spp. *Bulgaricus* strain CHCC16159.
St: *Streptococcus thermophilus*.

As will appear from the results, strains CHCC16731 and CHCC19216 when used as sole *S. thermophilus* in the culture blend produce a fermented milk product with a shear stress of 41.3 Pa and 51.5 Pa, respectively. When used in combination strains CHCC16731 and CHCC19216 produce a fermented milk product with a shear stress of 43.3 Pa.

This level of shear stress is high as compared to conventional sweetening strains as disclosed in e.g. WO2013/160413.

DEPOSITS AND EXPERT SOLUTIONS

The applicant requests that a sample of the deposited micro-organisms stated below may only be made available to an expert, until the date on which the patent is granted.

The strain *Streptococcus thermophilus* CHCC12339 has been deposited at Deutsche Sammlung von Mikroorganismen und Zellkulturen (DSMZ) GmbH, Inhoffenstr. 7B, D-38124 Braunschweig, Germany, on 10 Oct. 2010 under the accession No. DSM 24090.

The strain *Streptococcus thermophilus* CHCC11976 has been deposited at Deutsche Sammlung von Mikroorganismen und Zellkulturen (DSMZ) GmbH, Inhoffenstr. 7B, D-38124 Braunschweig, Germany, on 8 Sep. 2009 under the accession No. DSM 22934.

The strain *Streptococcus thermophilus* CHCC16731 has been deposited at Deutsche Sammlung von Mikroorganismen und Zellkulturen (DSMZ) GmbH, Inhoffenstr. 7B, D-38124 Braunschweig, Germany, on 4 Jun. 2014 under the accession No. DSM 28889.

The strain *Streptococcus thermophilus* CHCC19216 has been deposited at Deutsche Sammlung von Mikroorganismen und Zellkulturen (DSMZ) GmbH, Inhoffenstr. 7B, D-38124 Braunschweig, Germany, on 8 Dec. 2015 under the accession No. DSM 32227.

The strain *Lactobacillus delbrueckii* subsp. *bulgaricus* CHCC16159 has been deposited at Deutsche Sammlung von Mikroorganismen und Zellkulturen (DSMZ) GmbH, Inhoffenstr. 7B, D-38124 Braunschweig, Germany, on 6 Sep. 2012 under the accession No. DSM 26420.

The strain *Lactobacillus delbrueckii* subsp. *bulgaricus* CHCC16160 has been deposited at Deutsche Sammlung von Mikroorganismen und Zellkulturen (DSMZ) GmbH, Inhoffenstr. 7B, D-38124 Braunschweig, Germany, on 6 Sep. 2012 under the accession No. DSM 26421.

The deposits were made according to the Budapest treaty on the international recognition of the deposit of microorganisms for the purposes of patent procedure.

REFERENCES

WO2011/026863
WO2011/092300
WO2013/160413
Pool et al. (2006) Metabolic Engineering 8(5); 456-464
Thompson et al. (1985) J. Bacteriol. 162(1); 217-223
Chervaux et al. (2000). Appl and Environ Microbiol, 66, 5306-5311
Cochu et al. (2003). Appl and Environ Microbiol, 69(9), 5423-5432
Høier et al. (2010) in The Technology of Cheesemaking, 2nd Ed. Blackwell Publishing, Oxford; 166-192.

The invention claimed is:

1. A mutant *Streptococcus thermophilus* strain, wherein the strain is galactose-fermenting, wherein the strain carries a mutation in a DNA sequence of a glcK gene encoding a glucokinase protein, wherein the mutation inactivates the glucokinase protein or has a negative effect on expression of the glcK gene, wherein the strain is unable to metabolize glucose;

wherein the strain carries a mutation in a promoter region of a Galk gene encoding a galactokinase protein; and wherein the strain carries a mutation in a gene encoding a protein involved in transport of glucose into a cell of the strain, wherein the strain is unable to transport glucose across a cell membrane of the cell into the cell, with the proviso that the strain is not the *Streptococcus thermophilus* strain CHCC16731 that was deposited at Deutsche Sammlung von Mikroorganismen and Zellkulturen under accession No. DSM 28889.

2. The mutant *Streptococcus thermophilus* strain according to claim 1, wherein the strain is 2-deoxyglucose resistant.

3. The mutant *Streptococcus thermophilus* strain according to claim 1, wherein the strain increases an amount of glucose in 9.5% B-milk to at least 5 mg/ml when inoculated into the 9.5% B-milk at a concentration of $10^6$-$10^7$ CFU/ml and grown at 40° C. for 20 hours.

4. The mutant *Streptococcus thermophilus* strain according to claim 1, wherein the strain increases an amount of glucose in 9.5% B-milk with 0.05% sucrose to at least 5 mg/ml when inoculated into the 9.5% B-milk with 0.05% sucrose at a concentration of $10^6$-$10^7$ CFU/ml and grown at 40° C. for 20 hours.

5. The mutant *Streptococcus thermophilus* strain according to claim 1, wherein the strain carries a mutation in the promoter region of the GalK gene downstream of a −10 promoter box (Pribnow box).

6. The mutant *Streptococcus thermophilus* strain according to claim 1, wherein the mutation in the promoter region of the GalK gene is a mutation in a −10 promoter box.

7. The mutant *Streptococcus thermophilus* strain according to claim 1, wherein the strain generates a texture in fermented milk greater than about 40 Pa measured as shear stress after 12 hours of growth at 37° C.

8. A composition comprising from $10^4$ to $10^{12}$ CFU/g of the mutant *Streptococcus thermophilus* strain according to claim 1.

9. A method for producing a fermented milk product comprising inoculating and fermenting a milk substrate with at least one mutant *Streptococcus thermophilus* strain according to claim 1.

10. A fermented milk product comprising at least one mutant *Streptococcus thermophilus* strain according to claim 1.

11. The method of claim 9, wherein the method increases both sweetness and texture in the fermented milk product.

12. The method of claim 9, further comprising inoculating and fermenting the milk substrate with a *Lactobacillus delbrueckii* subsp. *bulgaricus* strain, wherein the method increases both sweetness and viscosity in the fermented milk product.

13. A *Streptococcus thermophilus* strain, wherein the strain is selected from the *Streptococcus thermophilus* CHCC19216 strain deposited at Deutsche Sammlung von Mikroorganismen and Zellkulturen under accession No. DSM 32227, and mutant strains derived therefrom, wherein the mutant strains are obtained by using the deposited strain as starting material, and wherein the mutant strains have a retained or further improved texturizing property and glucose secreting property as said deposited strain.

14. A composition comprising from $10^4$ to $10^{12}$ CFU/g of the *Streptococcus thermophilus* strain according to claim 9.

15. A method for producing a fermented milk product comprising inoculating and fermenting a milk substrate with at least one *Streptococcus thermophilus* strain according to claim 9.

16. A fermented milk product comprising at least one *Streptococcus thermophilus* strain according to claim 9.

17. The method of claim 15, wherein the method increases both sweetness and texture in the fermented milk product.

18. The method of claim 15, further comprising inoculating and fermenting the milk substrate with a *Lactobacillus delbrueckii* subsp. *bulgaricus* strain, wherein the method increases both sweetness and viscosity in the fermented milk product.

* * * * *

SEQUENCE LISTING

```
<160> NUMBER OF SEQ ID NOS: 6

<210> SEQ ID NO 1
<211> LENGTH: 966
<212> TYPE: DNA
<213> ORGANISM: Streptococcus thermophilus

<400> SEQUENCE: 1

atgagtaaga aactcttagg tattgacctt ggtggaacaa ctgttaagtt tggtattttg      60

actgcagatg gtgaagttca agaaaaatgg gctattgaaa caaatacgtt tgaaaatggt     120

agccacattg ttcctgacat tgtagaatct ttgaaacacc gtttggaatt gtatggactt     180

actgctgaag attttattgg aattggtatg ggatctccag gtgcagttga ccgagaaaat     240

aaaacagtaa cgggtgcctt taacttgaac tgggcagaaa ctcaagaagt tggctctgtt     300

attgaaaaag aacttggtat tccattcgct attgataatg atgctaatgt ggctgcactg     360

ggtgaacgtt gggttggtgc tggtgctaac aatcggaatg ttgtctttat aacattgggt     420

acaggtgttg gtggcggtgt tatcgctgat ggtaacttaa ttcatggtgt tgccggtgct     480
```

```
ggtggggaaa ttggtcacat tattgttgaa cctgacacag gatttgagtg tacttgcgga    540

aacaaggggt gtctggaaac tgtagcttca gcaacaggta ttgtacgtgt agcacatcat    600

ttggcagaaa aatacgaagg aaactcttct attaaagctg ctgtagacaa tggtgagttt    660

gtgacaagta aagatattat cgtagctgct actgaaggtg ataagtttgc tgacagcatt    720

gttgataaag tctctaaata cctcagactt gcaacagcaa acatctcaaa cattcttaac    780

ccagattctg tcgttatcgg tggtggtgtt tctgccgcag gagaattctt gcgtagtcgt    840

gttgaaggat actttacacg ttatgcattc ccacaagttc gccgtacaac aaaagtgaaa    900

ttagcggagc ttggaaatga tgcaggaatc attggagctg ctagtcttgc ttatagtatt    960

gacaaa                                                               966
```

<210> SEQ ID NO 2
<211> LENGTH: 322
<212> TYPE: PRT
<213> ORGANISM: Streptococcus thermophilus

<400> SEQUENCE: 2

```
Met Ser Lys Lys Leu Leu Gly Ile Asp Leu Gly Gly Thr Thr Val Lys
1               5                   10                  15

Phe Gly Ile Leu Thr Ala Asp Gly Glu Val Gln Glu Lys Trp Ala Ile
            20                  25                  30

Glu Thr Asn Thr Phe Glu Asn Gly Ser His Ile Val Pro Asp Ile Val
        35                  40                  45

Glu Ser Leu Lys His Arg Leu Glu Leu Tyr Gly Leu Thr Ala Glu Asp
    50                  55                  60

Phe Ile Gly Ile Gly Met Gly Ser Pro Gly Ala Val Asp Arg Glu Asn
65                  70                  75                  80

Lys Thr Val Thr Gly Ala Phe Asn Leu Asn Trp Ala Glu Thr Gln Glu
                85                  90                  95

Val Gly Ser Val Ile Glu Lys Glu Leu Gly Ile Pro Phe Ala Ile Asp
            100                 105                 110

Asn Asp Ala Asn Val Ala Ala Leu Gly Glu Arg Trp Val Gly Ala Gly
        115                 120                 125

Ala Asn Asn Arg Asn Val Val Phe Ile Thr Leu Gly Thr Gly Val Gly
    130                 135                 140

Gly Gly Val Ile Ala Asp Gly Asn Leu Ile His Gly Val Ala Gly Ala
145                 150                 155                 160

Gly Gly Glu Ile Gly His Ile Ile Val Glu Pro Asp Thr Gly Phe Glu
                165                 170                 175

Cys Thr Cys Gly Asn Lys Gly Cys Leu Glu Thr Val Ala Ser Ala Thr
            180                 185                 190

Gly Ile Val Arg Val Ala His His Leu Ala Glu Lys Tyr Glu Gly Asn
        195                 200                 205

Ser Ser Ile Lys Ala Ala Val Asp Asn Gly Glu Phe Val Thr Ser Lys
    210                 215                 220

Asp Ile Ile Val Ala Ala Thr Glu Gly Asp Lys Phe Ala Asp Ser Ile
225                 230                 235                 240

Val Asp Lys Val Ser Lys Tyr Leu Arg Leu Ala Thr Ala Asn Ile Ser
                245                 250                 255

Asn Ile Leu Asn Pro Asp Ser Val Val Ile Gly Gly Gly Val Ser Ala
            260                 265                 270

Ala Gly Glu Phe Leu Arg Ser Arg Val Glu Gly Tyr Phe Thr Arg Tyr
```

```
        275                 280                 285

Ala Phe Pro Gln Val Arg Arg Thr Thr Lys Val Lys Leu Ala Glu Leu
    290                 295                 300

Gly Asn Asp Ala Gly Ile Ile Gly Ala Ala Ser Leu Ala Tyr Ser Ile
305                 310                 315                 320

Asp Lys


<210> SEQ ID NO 3
<211> LENGTH: 909
<212> TYPE: DNA
<213> ORGANISM: Streptococcus thermophilus

<400> SEQUENCE: 3

atggctgaaa aaattcaatt atctcaagcg gatcgtaaaa aggtttggtg gcgctcacaa     60

ttcttgcaag gtgcatggaa ctatgaacgt atgcaaaact tgggttgggc ttactcactc    120

attcctgcta tcaaaaaact ttatactaac aaagaggacc aagccgcagc tcttaaacgt    180

cacttggaat tcttcaacac tcacccttac gtagctgctc ctatcatagg ggttccctta    240

gctcttgaag aagaaaaagc taatggtact gaaatcgaag atgcggctat ccaaggggtt    300

aaaatcggta tgatgggtcc acttgccggt atcggtgacc ctgtcttctg gttcacaatt    360

cgtccaattc ttggtgccct tggtgcatca ttggcacaag ctggtaacat tgctggtcca    420

cttatcttct tcattggttg gaaccttatc cgcatggcct tcttgtggta cactcaagaa    480

cttggttaca aagcaggttc agaaatcact aaagacatat ctggtggtat cttgaaagat    540

attactaaag ggcatcaat acttggtatg ttcatcttgg ccgtcctcgt tgaacgttgg    600

gtatctgtcg tcttcactgt aaagcttcca ggtaaagttt tgcctaaagg tgcttatatt    660

gaatggccaa aaggatatgt tactggtgac caactaaaaa ctatccttgg tcaagtcaac    720

gataagctta gctttgataa gattcaagtc gataccctac aaaaacaatt ggattcatta    780

attccaggtt tgacgggact tctccttact tttgcatgta tgtggttgct taagaagaaa    840

gtttcaccaa tcacaatcat catcggactc tttgtagttg gtattattgc aagcttcttc    900

ggaatcatg                                                            909


<210> SEQ ID NO 4
<211> LENGTH: 303
<212> TYPE: PRT
<213> ORGANISM: Streptococcus thermophilus

<400> SEQUENCE: 4

Met Ala Glu Lys Ile Gln Leu Ser Gln Ala Asp Arg Lys Lys Val Trp
1               5                   10                  15

Trp Arg Ser Gln Phe Leu Gln Gly Ala Trp Asn Tyr Glu Arg Met Gln
            20                  25                  30

Asn Leu Gly Trp Ala Tyr Ser Leu Ile Pro Ala Ile Lys Lys Leu Tyr
        35                  40                  45

Thr Asn Lys Glu Asp Gln Ala Ala Ala Leu Lys Arg His Leu Glu Phe
    50                  55                  60

Phe Asn Thr His Pro Tyr Val Ala Ala Pro Ile Ile Gly Val Pro Leu
65                  70                  75                  80

Ala Leu Glu Glu Glu Lys Ala Asn Gly Thr Glu Ile Glu Asp Ala Ala
                85                  90                  95

Ile Gln Gly Val Lys Ile Gly Met Met Gly Pro Leu Ala Gly Ile Gly
            100                 105                 110
```

```
Asp Pro Val Phe Trp Phe Thr Ile Arg Pro Ile Leu Gly Ala Leu Gly
        115                 120                 125

Ala Ser Leu Ala Gln Ala Gly Asn Ile Ala Gly Pro Leu Ile Phe Phe
    130                 135                 140

Ile Gly Trp Asn Leu Ile Arg Met Ala Phe Leu Trp Tyr Thr Gln Glu
145                 150                 155                 160

Leu Gly Tyr Lys Ala Gly Ser Glu Ile Thr Lys Asp Ile Ser Gly Gly
                165                 170                 175

Ile Leu Lys Asp Ile Thr Lys Gly Ala Ser Ile Leu Gly Met Phe Ile
            180                 185                 190

Leu Ala Val Leu Val Glu Arg Trp Val Ser Val Val Phe Thr Val Lys
        195                 200                 205

Leu Pro Gly Lys Val Leu Pro Lys Gly Ala Tyr Ile Glu Trp Pro Lys
    210                 215                 220

Gly Tyr Val Thr Gly Asp Gln Leu Lys Thr Ile Leu Gly Gln Val Asn
225                 230                 235                 240

Asp Lys Leu Ser Phe Asp Lys Ile Gln Val Asp Thr Leu Gln Lys Gln
                245                 250                 255

Leu Asp Ser Leu Ile Pro Gly Leu Thr Gly Leu Leu Leu Thr Phe Ala
            260                 265                 270

Cys Met Trp Leu Leu Lys Lys Lys Val Ser Pro Ile Thr Ile Ile Ile
        275                 280                 285

Gly Leu Phe Val Val Gly Ile Ile Ala Ser Phe Phe Gly Ile Met
    290                 295                 300
```

<210> SEQ ID NO 5
<211> LENGTH: 828
<212> TYPE: DNA
<213> ORGANISM: Streptococcus thermophilus

<400> SEQUENCE: 5

```
atgtcagata tgtcaattat ttctgcgatt ttggtcgtag ctgttgcctt ccttgctggt     60

cttgaaagta tccttgacca attccaattc caccaaccac ttgttgcatg taccctcatc    120

ggtgctgcca caggtaacct cactgcaggt atcatgcttg gtggttctct tcaaatgatt    180

acccttgctt gggcaaacat cggtgctgcc gtagctcctg acgttgccct tgcatctgtt    240

gccgctgcca tcattttggt taaaggtggt aaatttacag ctgaaggtat cggtgttgcg    300

attgcaatag ctatcctgct tgcagttgca ggtctcttcc taactatgcc tgttcgtaca    360

gcatctattg cctttgttca tgctgcagat aaagctgcag aacacggaaa catcgctggt    420

gttgaacgtg catactacct cgctctcctt cttcaaggtt tgcgtattgc tgtgccagca    480

gcccttcttc ttgccatccc ggcccaatct gttcaacatg cccttggctt gatgcctgac    540

tggctcaccc atggtttggt tgtcggtggt ggtatggtcg tagccgttgg ttacgccatg    600

attatcaata tgatggctac tcgtgaagtt tggccattct tcgccattgg ttttgctttg    660

gcagcaatta gccaattgac acttatcgct cttagtacca ttggtgttgc catcgccttc    720

atctacctca acctttctaa acaaggtggc ggaaatggtg gcggaaatgg tggcggaact    780

tcatctggtt caggcgaccc aatcggcgat atcttggaag actactag                828
```

<210> SEQ ID NO 6
<211> LENGTH: 275
<212> TYPE: PRT
<213> ORGANISM: Streptococcus thermophilus

<400> SEQUENCE: 6

-continued

```
Met Ser Asp Met Ser Ile Ile Ser Ala Ile Leu Val Val Ala Val Ala
1               5                   10                  15

Phe Leu Ala Gly Leu Glu Ser Ile Leu Asp Gln Phe Gln Phe His Gln
            20                  25                  30

Pro Leu Val Ala Cys Thr Leu Ile Gly Ala Ala Thr Gly Asn Leu Thr
        35                  40                  45

Ala Gly Ile Met Leu Gly Gly Ser Leu Gln Met Ile Thr Leu Ala Trp
    50                  55                  60

Ala Asn Ile Gly Ala Ala Val Ala Pro Asp Val Ala Leu Ala Ser Val
65                  70                  75                  80

Ala Ala Ala Ile Ile Leu Val Lys Gly Gly Lys Phe Thr Ala Glu Gly
                85                  90                  95

Ile Gly Val Ala Ile Ala Ile Ala Ile Leu Leu Ala Val Ala Gly Leu
            100                 105                 110

Phe Leu Thr Met Pro Val Arg Thr Ala Ser Ile Ala Phe Val His Ala
        115                 120                 125

Ala Asp Lys Ala Ala Glu His Gly Asn Ile Ala Gly Val Glu Arg Ala
    130                 135                 140

Tyr Tyr Leu Ala Leu Leu Leu Gln Gly Leu Arg Ile Ala Val Pro Ala
145                 150                 155                 160

Ala Leu Leu Leu Ala Ile Pro Ala Gln Ser Val Gln His Ala Leu Gly
                165                 170                 175

Leu Met Pro Asp Trp Leu Thr His Gly Leu Val Val Gly Gly Gly Met
            180                 185                 190

Val Val Ala Val Gly Tyr Ala Met Ile Ile Asn Met Met Ala Thr Arg
        195                 200                 205

Glu Val Trp Pro Phe Phe Ala Ile Gly Phe Ala Leu Ala Ala Ile Ser
    210                 215                 220

Gln Leu Thr Leu Ile Ala Leu Ser Thr Ile Gly Val Ala Ile Ala Phe
225                 230                 235                 240

Ile Tyr Leu Asn Leu Ser Lys Gln Gly Gly Gly Asn Gly Gly Gly Asn
                245                 250                 255

Gly Gly Gly Thr Ser Ser Gly Ser Gly Asp Pro Ile Gly Asp Ile Leu
            260                 265                 270

Glu Asp Tyr
        275
```